United States Patent
Gotoh et al.

(10) Patent No.: US 11,299,712 B2
(45) Date of Patent: Apr. 12, 2022

(54) METHOD FOR INDUCING DIFFERENTIATION OF ALVEOLAR EPITHELIAL CELLS

(71) Applicant: KYOTO UNIVERSITY, Kyoto (JP)

(72) Inventors: Shimpei Gotoh, Kyoto (JP); Yuki Yamamoto, Kyoto (JP); Satoshi Konishi, Kyoto (JP); Michiaki Mishima, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 85 days.

(21) Appl. No.: 15/555,183

(22) PCT Filed: Mar. 2, 2016

(86) PCT No.: PCT/JP2016/057254
§ 371 (c)(1),
(2) Date: Sep. 1, 2017

(87) PCT Pub. No.: WO2016/143803
PCT Pub. Date: Sep. 15, 2016

(65) Prior Publication Data
US 2018/0051256 A1   Feb. 22, 2018

(30) Foreign Application Priority Data
Mar. 6, 2015   (JP) .............................. JP2015-045298

(51) Int. Cl.
*C12N 5/071* (2010.01)

(52) U.S. Cl.
CPC ...... *C12N 5/0688* (2013.01); *C12N 2501/117* (2013.01); *C12N 2501/119* (2013.01); *C12N 2501/15* (2013.01); *C12N 2501/155* (2013.01); *C12N 2501/16* (2013.01); *C12N 2501/39* (2013.01); *C12N 2501/415* (2013.01); *C12N 2501/50* (2013.01); *C12N 2501/727* (2013.01); *C12N 2501/73* (2013.01); *C12N 2506/45* (2013.01); *C12N 2513/00* (2013.01)

(58) Field of Classification Search
None
See application file for complete search history.

(56) References Cited

U.S. PATENT DOCUMENTS

| 5,843,780 | A | 12/1998 | Thomson | |
|---|---|---|---|---|
| 2013/0122536 | A1 | 5/2013 | Osafune et al. | |
| 2013/0224116 | A1 | 8/2013 | Bonder et al. | |
| 2016/0068816 | A1* | 3/2016 | Osafune ............... | C12N 5/0688 435/377 |

FOREIGN PATENT DOCUMENTS

| EP | 2484754 A1 | 8/2012 | | |
|---|---|---|---|---|
| JP | 2014 023519 | 2/2014 | | |
| WO | 2007/069666 A1 | 6/2007 | | |
| WO | 2011/139628 A1 | 11/2011 | | |
| WO | 2014/018691 | 1/2014 | | |
| WO | WO-2014018691 A1 | * 1/2014 | ........... | C12N 5/0688 |
| WO | 2014/052458 A1 | 4/2014 | | |
| WO | 2014/168264 A1 | 10/2014 | | |
| WO | WO-2014168264 A1 | * 10/2014 | ........... | C12N 5/0688 |

OTHER PUBLICATIONS

Stemcell Technologies "CHIR99021: WNT pathway activator; Inhibits GSK3", available on the company's webpage <https://www.stemcell.com/chir99021.html>, copyright 2018, accessed Dec. 18, 2018 (Year: 2018).*
Geling et al. "A γ-secretase inhibitor blocks Notch signaling in vivo and causes a severe neurogenic phenotype in zebrafish." EMBO reports 3.7 (2002): 688-694. (Year: 2002).*
Sheppard "ROCKing pulmonary fibrosis." The Journal of Clinical Investigation 123.3 (2013): 1005-1006 (Year: 2013).*
Bone et al. "A novel chemically directed route for the generation of definitive endoderm from human embryonic stem cells based on inhibition of GSK-3." Journal of Cell Science 124.12 (2011): 1992-2000 (Year: 2011).*
Fujiwara et al. "Monoclonal antibody 7F9 recognizes rat protein homologous to human carboxypeptidase-M in developing and adult rat lung." Respirology 12.1 (2007): 54-62 (Year: 2007).*
Mancia et al. "Cryopreservation and in vitro culture of primary cell types from lung tissue of a stranded pygmy sperm whale (*Kogia breviceps*)." Comparative Biochemistry and Physiology Part C: Toxicology & Pharmacology 155.1 (2012): 136-142 (Year: 2012).*
Foster et al. "The Rho pathway mediates transition to an alveolar type I cell phenotype during static stretch of alveolar type II cells." Pediatric Research 67.6 (2010): 585 (Year: 2010).*
Kolla et al. "Thyroid transcription factor in differentiating type II cells: regulation, isoforms, and target genes." American Journal of Respiratory Cell and Molecular Biology 36.2 (2007): 213-225 (Year: 2007).*
Van der Velden et al. "LysoTracker is a marker of differentiated alveolar type II cells." Respiratory Research 14.1 (2013): 123 (Year: 2013).*

(Continued)

*Primary Examiner* — Emily A Cordas
(74) *Attorney, Agent, or Firm* — Lucas & Mercanti, LLP

(57) ABSTRACT

This invention provides a method for stably producing type II alveolar epithelial cells from pluripotent stem cells. Specifically, the invention relates to a method for producing type II alveolar epithelial cells from pluripotent stem cells comprising steps of: (1) culturing pluripotent stem cells in a medium containing activin A and a GSK3β inhibitor; (2) culturing the cells obtained in Step (1) in a medium containing a BMP inhibitor and a TGFβ inhibitor; (3) culturing the cells obtained in Step (2) in a medium containing BMP4, retinoic acid, and a GSK3β inhibitor; (4) culturing the ventral anterior foregut cells obtained in Step (3) in a medium containing a GSK3β inhibitor, FGF10, KGF, and a NOTCH signal inhibitor; and (5) subjecting the alveolar epithelial progenitor cells obtained in Step (4) to three-dimensional culture in a medium containing a steroid drug, a cAMP derivative, a phosphodiesterase inhibitor, and KGF.

14 Claims, 21 Drawing Sheets
(9 of 21 Drawing Sheet(s) Filed in Color)

(56) References Cited

OTHER PUBLICATIONS

Gotoh et al. "Generation of alveolar epithelial spheroids via isolated progenitor cells from human pluripotent stem cells." Stem cell reports 3.3 (Aug. 21, 2014): 394-403 (Year: 2014).*
A. L. Firth et al, "Generation of multiciliated cells in functional airway epithelia from human induced pluripotent stem cells," Proceedings of the National Academy of Sciences, Mar. 24, 2014, pp. E1723-E1730, vol. 111, No. 17.
Supplementary European Search Report issued in connection with corresponding European Patent Application No. 16761771.1, dated Jul. 27, 2018.
Rippon, H. J. et al, Cloning Stem Cells 6: 49-56, 2004.
Coraux, C. et al. Am. J. Respir. Cell Mol. Biol., 32:87-92, 2005.
Morrisey, E. E. and Hogan, B. L. M., Dev. Cell., 18: 8-23, 2010.
Ghaedi, M. et al., J. Clin. Invest., vol. 123, pp. 4950-4962, 2013.
Huang, S. X. et al., Nat. Biotechnol., vol. 32, pp. 84-91, 2014.
Gotoh, S. et al., Stem Cell Reports, 2014, vol. 3, pp. 394-403.
Dieteren et al., "Carboxypeptidase M: Multiple alliances and unknown partners", Clinica Chimica ACTA, 2009, vol. 399, No. 1-2, pp. 24-39.
EPO, Supplementary European Search Report issued in connection with the related European Application No. EP 14782957.6, dated Aug. 17, 2016 (4 pages).
Barkauskas et al., "Type 2 alveolar cells are stem cells in adult lung", J. Clin. Invest. 2013, vol. 123, No. 7, pp. 3025-3036.
Schmeckebier et al.,"Keratinocyte Growth Factor and Dexamethasone Plus Elevated cAMP Levels Synergistically Support Pluripotent Stem Cell Differentiation into Alveolar Epithelial Type II Cells", Tissue Engineering, 2013, vol. 19, No. 7-8, pp. 938-951.
Longmire et al., "Efficient Derivation of Purified Lung and Thyroid Progenitors from Embryonic Stem Cells", Cell Stem Cell, 2012, vol. 10, pp. 398-411.
Green et al., "Generation of anterior foregut endoderm from human embryonic and induced pluripotent stem cells", Nature Biotechnology, 2011, vol. 29, No. 3, pp. 267-272.
Mou et al., "Generation of Multipotent Lung and Airway Progenitors from Mouse ESCs and Patient-Specific Cystic Fibrosis iPSCs", Cell Stem Cell, 2012, vol. 10, pp. 385-397.
Norrman et al., "Distinct gene expression signatures in human embryonic stem cells differentiated towards definitive endoderm at single-cell level", Methods, 2012, vol. 59, pp. 59-70.
Williams, "Alveolar Type I Cells: Molecular Phenotype and Development", Annual Review of Physiology, 2003, vol. 65, pp. 669-695.
Horalkova et al., "Characterisation of the R3/1 cell line as an alveolar epithelial cell model for drug disposition studies", European Journal of Pharmaceutical Sciences, 2009, vol. 36, pp. 444-450.
Ikeda et al., "Differential expression of carboxypeptidase M during lung development", Cell Structure and Function, 2004, vol. 29, pp. 53.
ISA/JP, International Search Report dated Jul. 22, 2014, which was issued for International PCT Application No. PCT/JP2014/061106, along with English Translations (11 pages).
Giffin et al., "Alveolar Type II Cell-Fibroblast Interactions, Synthesis and Secretion of Surfactant and Type I Collagen", Journal of Cell Science, vol. 105, 1993, pp. 423-432.

* cited by examiner

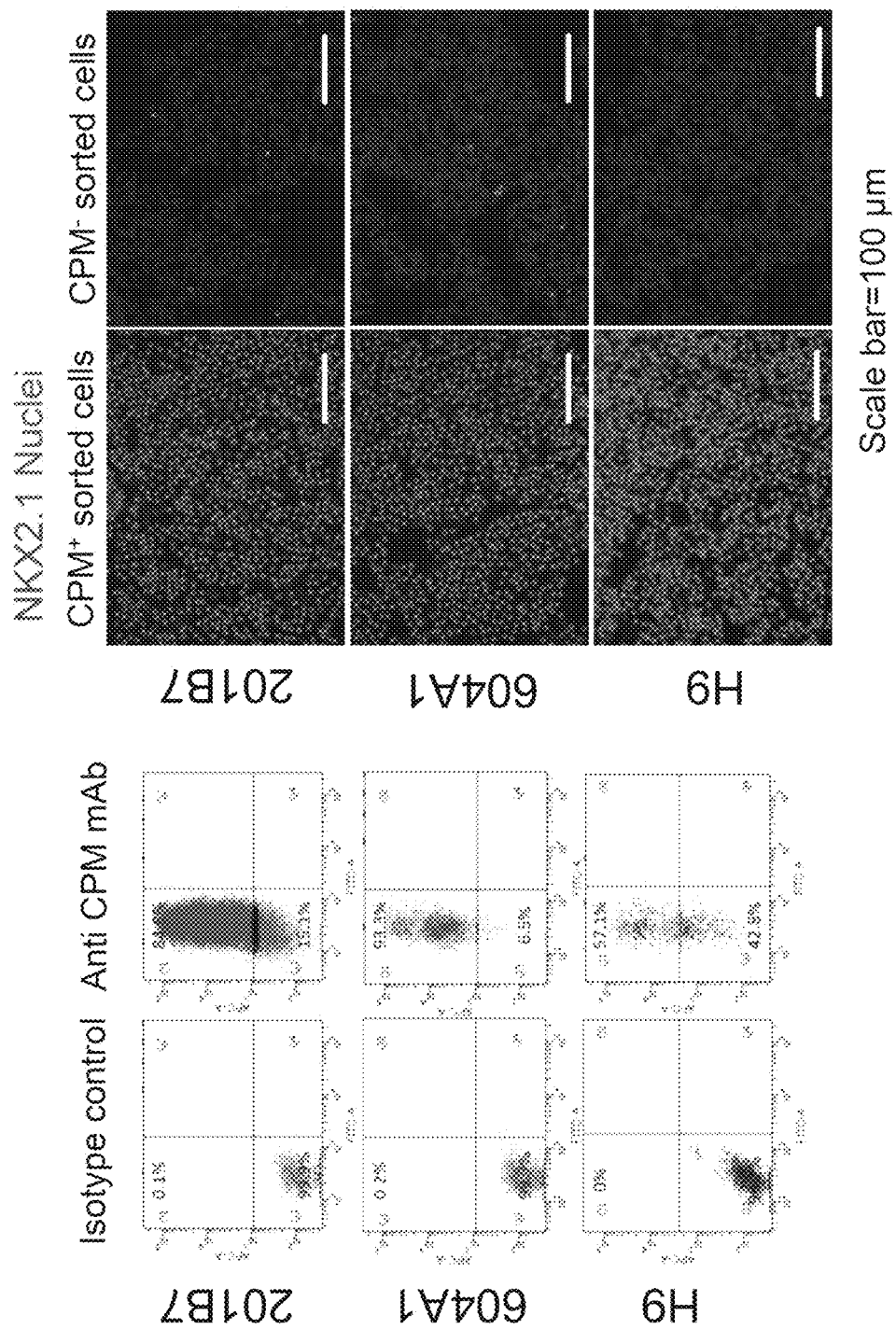

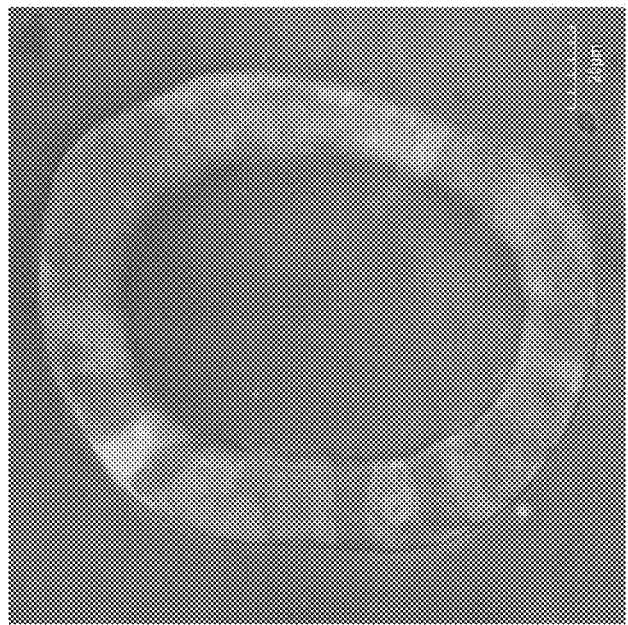
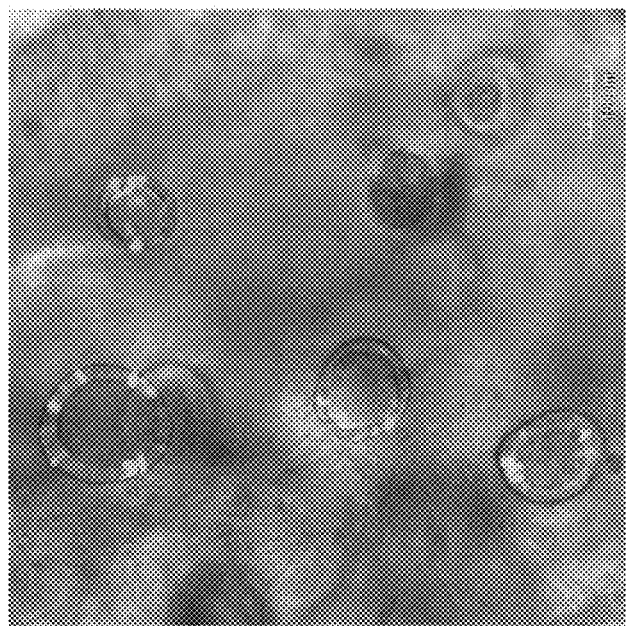
Fig. 6 CPM+ cell-derived spheroids (Day 35)

METHOD FOR INDUCING DIFFERENTIATION OF ALVEOLAR EPITHELIAL CELLS

CROSS-REFERENCE TO RELATED APPLICATIONS

This application is a 371 of PCT/JP2016/057254, filed Mar. 2, 2016, which claims the benefit of Japanese Patent Application No. 2015-045298, filed Mar. 6, 2015.

TECHNICAL FIELD

The present invention relates to a method for producing type II alveolar epithelial cells from pluripotent stem cells, a kit for producing type II alveolar epithelial cells from pluripotent stem cells, a method for type II alveolar epithelial cell culture, and a kit for type II alveolar epithelial cell culture, for example.

BACKGROUND ART

The lung is one of the most complicated organs, and it is considered to be composed of approximately 40 different types of cells. Among them, the pulmonary alveolus is composed of the alveolar space, which stores gas, and the alveolar epithelium, which surrounds the same. In addition, the alveolar epithelium is composed of the type I alveolar epithelial cells and the type II alveolar epithelial cells. The former forms a blood-air barrier with the microvascular endothelium surrounding the pulmonary alveolus with the aid of the basal membrane and exchanges the intra-alveolar gas with the blood gas. The latter comprises many lamellar corpuscles, it undergoes exocytosis of pulmonary surfactants, and it forms the alveolar lining layer.

In recent years, cells having pluripotency, such as embryonic stem cells (ES cells) or induced pluripotent stem cells (iPS cells) obtained by introducing undifferentiated-cell-specific genes into somatic cells, have been reported, methods for inducing alveolar epithelial cells from such cells have been reported (Rippon, H. J. et al, Cloning Stem Cells 6: 49-56, 2004; Coraux, C. et al, Am. J. Respir. Cell Mol. Biol., 32: 87-92, 2005; Morrisey, E. E. and Hogan, B. L. M., Dev. Cell., 18: 8-23, 2010; Ghaedi, M. et al., J. Clin. Invest., Vol. 123, pp. 4950-62, 2013; and Huang, S. X. et al., Nat. Biotechnol., Vol. 32, pp. 84-91, 2014), and growth factors and the like that are necessary for the induction of such cells have also been reported. However, there are no examples demonstrating the induction of human pulmonary alveolar cells with high reproducibility and efficiency.

The present inventors disclose that three-dimensional coculture of human pluripotent stem cells is useful for induction of differentiation into type II alveolar epithelial cells and a reporter enables isolation of type II alveolar epithelial cells (Gotoh, S. et al., Stem Cell Reports, 2014, Vol. 3, pp. 394-403). The present inventors also disclose a method for producing alveolar epithelial progenitor cells from pluripotent stem cells (WO 2014/168264).

SUMMARY OF THE INVENTION

It is an object of the present invention to provide a method for producing type II alveolar epithelial cells from pluripotent stem cells and a kit for producing type II alveolar epithelial cells from pluripotent stem cells. It is another object of the present invention to provide a method for type II alveolar epithelial cell culture and a kit for type II alveolar epithelial cell culture.

The present inventors have conducted concentrated studies in order to attain the above objects. As a result, they discovered that pluripotent stem cells could be induced to differentiate into type II alveolar epithelial cells with the use of various growth factors and compounds. This has led to the completion of the present invention.

Specifically, the present invention includes the following.

[1] A method for producing type II alveolar epithelial cells from pluripotent stem cells comprising Steps (1) to (5) below:
    (1) culturing pluripotent stem cells in a medium containing activin A and a GSK3β inhibitor;
    (2) culturing the cells obtained in Step (1) in a medium containing a BMP inhibitor and a TGFβ inhibitor;
    (3) culturing the cells obtained in Step (2) in a medium containing BMP4, retinoic acid, and a GSK3β inhibitor;
    (4) culturing the ventral anterior foregut cells obtained in Step (3) in a medium containing a GSK3β inhibitor, FGF10, KGF, and a NOTCH signal inhibitor; and
    (5) subjecting the alveolar epithelial progenitor cells obtained in Step (4) to three-dimensional culture in a medium containing a steroid drug, a cAMP derivative, a phosphodiesterase inhibitor, and KGF.

[2] The method according to [1], wherein the GSK3β inhibitor is CHIR99021, the BMP inhibitor is Noggin, the TGFβ inhibitor is SB431542, the NOTCH signal inhibitor is DAPT, the steroid drug is dexamethasone, the cAMP derivative is 8-Br-cAMP, and the phosphodiesterase inhibitor is 3-isobutyl-1-methylxanthine (IBMX).

[3] The method according to [1] or [2], wherein Step (1) comprises culturing pluripotent stem cells in a medium further supplemented with a ROCK inhibitor and/or a HDAC inhibitor.

[4] The method according to [3], wherein the ROCK inhibitor is Y-27632 and/or the HDAC inhibitor is sodium butyrate.

[5] The method according to any one of [1] to [4], which further comprises, following Step (4), a step of isolating CPM-positive cells as alveolar epithelial progenitor cells.

[6] The method according to any one of [1] to [5], wherein, following Step (4), the alveolar epithelial progenitor cells are cryopreserved and the alveolar epithelial progenitor cells cultured in Step (5) are obtained by thawing the cryopreserved alveolar epithelial progenitor cells.

[7] The method according to any one of [1] to [6], wherein Step (5) comprises subjecting alveolar epithelial progenitor cells to three-dimensional culture in a medium further supplemented with a ROCK inhibitor.

[8] The method according to [7], wherein the ROCK inhibitor is Y-27632.

[9] The method according to any one of [1] to [8], which further comprises, following Step (5), a step of isolating cells positive for one or more type II alveolar epithelial cell markers selected from the group consisting of SFTPC, EpCAM, and CEACAM6 as type II alveolar epithelial cells.

[10] The method according to [9], wherein the cells further positive for staining of acidic fractions for live cells are isolated as type II alveolar epithelial cells.

[11] The method according to any one of [1] to [10], wherein, following Step (5), the type II alveolar epithelial cells obtained are cryopreserved.

[12] A kit for producing type II alveolar epithelial cells from pluripotent stem cells comprising activin A, a GSK3β inhibitor, a BMP inhibitor, a TGFβ inhibitor, BMP4, retinoic acid, FGF10, KGF, a NOTCH signal inhibitor, a steroid drug, a cAMP derivative, and a phosphodiesterase inhibitor.

[13] The kit according to [12], wherein the GSK3β inhibitor is CHIR99021, the BMP inhibitor is Noggin, the TGFβ inhibitor is SB431542, the NOTCH signal inhibitor is DAPT, the steroid drug is dexamethasone, the cAMP derivative is 8-Br-cAMP, and the phosphodiesterase inhibitor is IBMX.

[14] The kit according to [12] or [13], which further comprises a ROCK inhibitor and/or a HDAC inhibitor.

[15] The kit according to [14], wherein the ROCK inhibitor is Y-27632 and/or the HDAC inhibitor is sodium butyrate.

[16] A method for type II alveolar epithelial cell culture comprising a step of subjecting type II alveolar epithelial cells to three-dimensional culture in a medium containing a steroid drug, a cAMP derivative, a phosphodiesterase inhibitor, and KGF.

[17] The method according to [16], wherein the steroid drug is dexamethasone, the cAMP derivative is 8-Br-cAMP, and the phosphodiesterase inhibitor is IBMX.

[18] The method according to [16] or [17], which comprises subjecting type II alveolar epithelial cells to three-dimensional culture in a medium further supplemented with a ROCK inhibitor.

[19] The method according to [18], wherein the ROCK inhibitor is Y-27632.

[20] The method according to any one of [16] to [19], which comprises subjecting type II alveolar epithelial cells to three-dimensional culture in a medium further supplemented with a WNT signal inhibitor and/or IGF2.

[21] The method according to [20], wherein the WNT signal inhibitor is WIF1.

[22] The method according to any one of [16] to [21], wherein the type II alveolar epithelial cells are produced by the method according to any one of [1] to [11].

[23] A kit for type II alveolar epithelial cell culture comprising a steroid drug, a cAMP derivative, a phosphodiesterase inhibitor, and KGF.

[24] The kit according to [23], wherein the steroid drug is dexamethasone, the cAMP derivative is 8-Br-cAMP, and the phosphodiesterase inhibitor is IBMX.

[25] The kit according to [23] or [24], which further comprises a ROCK inhibitor.

[26] The kit according to [25], wherein the ROCK inhibitor is Y-27632.

[27] The kit according to any one of [23] to [26], which further comprises the WNT signal inhibitor and/or IGF2.

[28] The kit according to [27], wherein the WNT signal inhibitor is WIF1.

This description includes part or all of the content as disclosed in Japanese Patent Application No. 2015-045298, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2C and 2D are continued from FIGS. 2A and 2B.

FIG. 6 shows photographs demonstrating the results of observation of spheroids formed from CPM$^+$ cells on Day 35 (i.e., upon completion of Step 5) in a high-power field.

EMBODIMENTS FOR CARRYING OUT THE INVENTION

Figure 1:
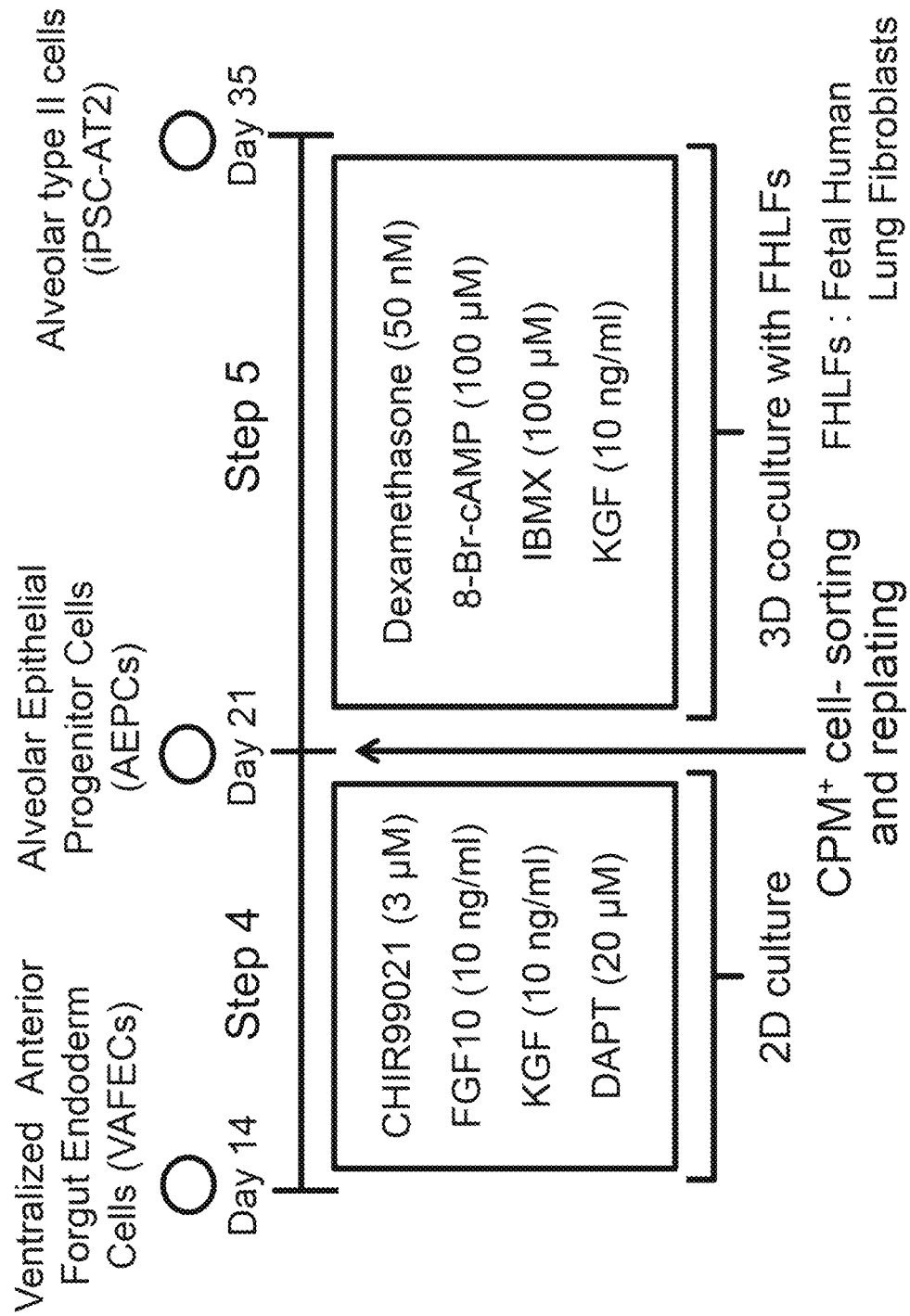
FIG. 1 shows a method for inducing type II alveolar epithelial cells from ventral anterior foregut cells using human pluripotent stem cells.

[Method for Producing Type II Alveolar Epithelial Cells from Pluripotent Stem Cells]

The method for producing type II alveolar epithelial cells from pluripotent stem cells according to the present invention comprises Steps (1) to (5) below:

(1) culturing pluripotent stem cells in a medium containing activin A and a GSK3β inhibitor;

(2) culturing the cells obtained in Step (1) in a medium containing a BMP inhibitor and a TGFβ inhibitor;

(3) culturing the cells obtained in Step (2) in a medium containing BMP4, retinoic acid, and a GSK3β inhibitor;

(4) culturing the ventral anterior foregut cells obtained in Step (3) in a medium containing a GSK3β inhibitor, FGF10, KGF, and a NOTCH signal inhibitor; and (5) subjecting the alveolar epithelial progenitor cells obtained in Step (4) to three-dimensional culture in a medium containing a steroid drug, a cAMP derivative, a phosphodiesterase inhibitor, and KGF.

In the present invention, the term "ventral anterior foregut cells" refers to cells that are destined to differentiate into the thyroid gland or lung in the presence of developmentally appropriate stimuli, and such cells express NKX2-1, GATA6, and/or HOPX.

In the present invention, the term "alveolar epithelial progenitor cells" refers to progenitor cells of type I alveolar epithelial cells or type II alveolar epithelial cells, which express CPM and/or NKX2-1.

In the present invention, the term "type II alveolar epithelial cells" refers to epithelial cells that histologically produce pulmonary surfactants and have morphological features, such as lamellae and multivesicular bodies, in the cells. For example, SFTPA, SFTPB, SFTPC, SFTPD, EpCAM, CEACAM6, DC-LAMP, ABCA3, and LPCAT1 are expressed therein.

The steps of the method for producing type II alveolar epithelial cells from pluripotent stem cells according to the present invention are described below.

(1) Step of Culture in a Medium Containing Activin a and a GSK3β Inhibitor (Step 1)

A medium used in the step of pluripotent stem cell culture according to the present invention can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, NEUROBASAL® Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, GLUTAMAX™ (Invitrogen), nonessential amino acids, vitamins, growth factors, low-molecular-weight compounds, antibiotics, antioxidants, pyruvic acids, buffer agents, and inorganic salts. RPMI 1640 medium supplemented with B27 and antibiotics is preferable.

In this step, pluripotent stem cells are cultured in a medium prepared by supplementing the basal medium described above with activin A and a GSK3β inhibitor. In this step, a HDAC inhibitor may further be added.

Activin A is a homodimer with two beta A chains, the amino acid sequence of activin A is 100% homologous to that of a protein of a human, mouse, rat, pig, cow, or cat, and, accordingly, relevant species are not particularly limited. In the present invention, activin A is preferably of an active form with the N-terminal peptide being cleaved, and it is preferably a homodimer comprising, bound thereto via a disulfide bond, the Gly311-Ser426 fragment with the N-terminal peptide of the inhibin beta A chain (e.g., NCBI Accession Number NP_002183) being cleaved. Such activin A is commercially available from, for example, Wako and R&D Systems.

The activin A concentration in a medium is, for example, 10 ng/ml to 1 mg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, 300 ng/ml, 400 ng/ml, 500 ng/ml, 600 ng/ml, 700 ng/ml, 800 ng/ml, 900 ng/ml, or 1 mg/ml, although the concentration is not limited thereto. The concentration is preferably 100 ng/ml.

The term "GSK3β inhibitor" used herein is defined as a substance that inhibits kinase activity of the GSK-3β protein (e.g., the capacity for phosphorylation of β-catenin), and many such substances are already known. Examples thereof include: an indirubin derivative, such as BIO, which is also known as a GSK-3β inhibitor IX (6-bromoindirubin-3'-oxime); a maleimide derivative, such as SB216763 (3-(2,4-dichlorophenyl)-4-(1-methyl-1H-indol-3-yl)-1H-pyrrole-2, 5-dione); a phenyl α-bromomethylketone compound, such as a GSK-3β inhibitor VII (4-dibromoacetophenone); a cell-permeable phosphorylated peptide, such as L803-mts, which is also known as a GSK-3 (3 peptide inhibitor (i.e., Myr-N-GKEAPPAPPQSpP-NH$_2$); and CHIR99021, such as 6-[2-[4-(2,4-dichlorophenyl)-5-(4-methyl-1H-imidazol-2-yl)pyrimidin-2-ylamino]-ethylamino]pyridine-3-carbonitrile, with high selectivity. While such compounds are commercially available from, for example, Calbiochem or Biomol, and easily used, such compounds may be obtained from other companies, or persons may prepare such compounds by themselves.

A GSK-3β inhibitor that can be preferably used in the present invention is CHIR99021. In this step, the CHIR99021 concentration in a medium is, for example, 1 nM to 50 μM, and it is specifically 1 nM, 10 nM, 50 nM, 100 nM, 500 nM, 750 nM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. In this step, the concentration is preferably 1 µM.

The term "HDAC inhibitor" is defined as a substance that inhibits or inactivates enzyme activity of histone deacetylase (HDAC). Examples thereof include: low-molecular-weight inhibitors, such as valproic acid (VPA) (Nat. Biotechnol., 26 (7): 795-797, 2008), trichostatin A, sodium butyrate (NaB), MC 1293, and M344; nucleic acid-based expression inhibitors, such as siRNAs and shRNAs against HDAC (e.g., HDAC1 siRNA Smartpool® (Millipore) and HuSH 29mer shRNA Constructs against HDAC1 (OriGene)); and DNA methyltransferase inhibitors (e.g., 5'-azacytidine) (Nat. Biotechnol., 26 (7): 795-797, 2008).

An HDAC inhibitor that can be preferably used in the present invention is sodium butyrate (NaB). The sodium butyrate (NaB) concentration in a medium is, for example, 1 µM to 5 mM, and it is specifically 1 µM, 10 µM, 50 µM, 100 µM, 125 µM, 250 µM, 500 µM, 750 µM, 1 mM, 2 mM, 3 mM, 4 mM, or 5 mM, although the concentration is not limited thereto. The concentration is preferably 125 µM to 250 µm.

In this step, culture may be conducted in a culture vessel treated with a coating agent. A coating agent may be a naturally occurring or artificially synthesized extracellular matrix. Examples thereof include BD MATRIGEL®, collagen, gelatin, laminin, heparan sulfate proteoglycan, entactin, and a combination of any thereof, with MATRIGEL® being preferable.

This step may comprise a process of pluripotent stem cell detachment.

Examples of methods for cell detachment include a method of mechanical detachment and a method of cell detachment involving the use of a cell detachment solution having protease activity and collagenase activity (e.g., Accutase™ and Accumax™) or a cell detachment solution having collagenase activity alone. It is preferable that human pluripotent stem cells be detached with the use of a cell detachment solution having protease activity and collagenase activity, with the use of Accutase™ being particularly preferable.

When the step comprises a process of cell detachment, a ROCK inhibitor may be added to a medium, so as to inhibit pluripotent stem cell death caused by detachment.

An ROCK inhibitor is not particularly limited, provided that it can inhibit functions of Rho kinase (ROCK). Examples thereof include: Y-27632 ((+)-(R)-trans-4-(1-aminoethyl)-N-(4-pyridyl)cyclohexanecarboxamide dihydrochloride) (e.g., Ishizaki et al., Mol. Pharmacol., 57, 976-983, 2000; Narumiya et al., Methods Enzymol., 325, 273-284, 2000); Fasudil/HA1077 (e.g., Uenata et al., Nature 389: 990-994, 1997); H-1152 (e.g., Sasaki et al., Pharmacol. Ther., 93: 225-232, 2002); Wf-536 (e.g., Nakajima et al., Cancer Chemother. Pharmacol., 52 (4): 319-324, 2003) and derivatives thereof; antisense nucleic acids against ROCK; RNA interference-inducible nucleic acids (e.g., siRNA); dominant-negative variants; and expression vectors thereof. Since other low-molecular-weight compounds are known as ROCK inhibitors, such compounds and derivatives thereof can also be used in the present invention (e.g., U.S. Patent Application Publication Nos. 2005/0209261, 2005/0192304, 2004/0014755, 2004/0002508, 2004/0002507, 2003/0125344, and 2003/0087919, WO 2003/062227, WO 2003/059913, WO 2003/062225, WO 2002/076976, and WO 2004/039796). In the present invention, one or more types of ROCK inhibitors can be used.

An ROCK inhibitor that can be preferably used in the present invention is Y-27632. The Y-27632 concentration is, for example, 100 nM to 50 µM, and it is specifically 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. The concentration is preferably 10 µM.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 3 days, 4 days, 5 days, 6 days, 7 days, 8 days, 9 days, 10 days, 11 days, or 12 days. The culture period is preferably at least 6 days, and it is particularly preferably 6 days. When the ROCK inhibitor is added, the duration of addition is 1 day or 2 days, and preferably 2 days. When the HDAC inhibitor is further added, such addition is initiated on the day following the initiation of the step, and culture is conducted for at least 3 days, 4 days, 5 days, 6 days, 7 days, 8 days, 9 days, 10 days, or 11 days. Culture is preferably conducted for at least 5 days, and particularly preferably for 5 days, in the presence of the HDAC inhibitor.

(2) Step of Culture in a Medium Containing a BMP Inhibitor and a TGFβ Inhibitor (Step 2)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, NEUROBASAL® Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, GLUTAMAX™ (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with GLUTAMAX™, B27, N2, 3'-thiol glycerol, and ascorbic acid is preferable.

In this step, the cells obtained in the previous step (i.e., the step of pluripotent stem cell culture in a medium containing activin A and a GSK3β inhibitor) are cultured in a medium prepared by supplementing the basal medium with a BMP inhibitor and a TGFβ inhibitor.

Examples of BMP inhibitors include: protein-based inhibitors, such as Chordin, Noggin, and Follistatin; dorsomorphin (i.e., 6-[4-(2-piperidin-1-yl-ethoxy)phenyl]-3-pyridin-4-yl-pyrazolo[1,5-a]pyrimidine) and a derivative thereof (P. B. Yu et al., 2007, Circulation, 116: II_60; P. B. Yu et al., 2008, Nat. Chem. Biol., 4: 33-41; J. Hao et al., 2008, PLoS ONE, 3 (8): e2904); and LDN-193189 (i.e., 4-(6-(4-(piperazin-1-yl)phenyl)pyrazolo[1,5-a]pyrimidin-3-yl)quinoline). Dorsomorphin and LDN-193189 are commercially available from Sigma-Aldrich and Stemgent, respectively.

A BMP inhibitor that can be preferably used in the present invention is Noggin. The Noggin concentration in a medium is not particularly limited, provided that BMP can be inhibited. For example, such concentration is 1 ng/ml to 2 µg/ml, and it is specifically 1 ng/ml, 10 ng/ml, 50 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1 µg/ml, or 2 µg/ml. The concentration is preferably 100 ng/ml.

The term "TGFβ inhibitor" used herein refers to a substance that inhibits signal transmission from the binding of TGFβ to a receptor leading to SMAD. A TGFβ inhibitor is not particularly limited, provided that such substance inhibits TGFβ from binding to a receptor; i.e., the ALK family, or such substance inhibits phosphorylation of SMAD caused by the ALK family. Examples thereof include Lefty-1 (e.g., NCBI Accession Nos. mouse NM_010094 and human NM_020997), SB431542 (4-(4-(benzo[d][1,3]dioxol-5-yl)-5-(pyridin-2-yl)-1H-imidazol-2-yl)benzamide), SB202190 (R. K. Lindemann et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (WO 2009/146408), and derivatives thereof.

A TGFβ inhibitor that can be preferably used in the present invention is SB431542. The SB431542 concentration in a medium is not particularly limited, provided that TGFβ is inhibited. For example, such concentration is 1 µM to 500 µM, and it is specifically 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 60 µM, 70 µM, 80 µM, 90 µM, 100 µM, 200 µM, 300 µM, 400 µM, or 500 µM. The concentration is preferably 10 µM.

In this step, culture may be conducted in a culture vessel treated with a coating agent. Examples of coating agents include BD MATRIGEL®, collagen, gelatin, laminin, heparan sulfate proteoglycan, entactin, and a combination of any thereof, with MATRIGEL® being preferable.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, SOX17- and/or FOXA2-positive cells may be selected and used in this step. This method is preferably implemented by means of media exchange.

When the step comprises a process of cell detachment, a ROCK inhibitor may be added to a culture solution, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 1 day, 2 days, 3 days, 4 days, 5 days, 6 days, 7 days, or 8 days. The culture period is preferably 4 days.

(3) Step of Culture in a Medium Containing BMP4, Retinoic Acid, and a GSK3β Inhibitor (Step 3)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, NEUROBASAL® Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, GLUTAMAX™ (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with GLUTAMAX™, B27, N2, 3'-thiol glycerol, and ascorbic acid is preferable.

In this step, the cells obtained in the previous step (i.e., the step of culture in a medium containing a BMP inhibitor and a TGFβ inhibitor) are cultured in a medium prepared by supplementing the basal medium with BMP4, retinoic acid, and a GSK3β inhibitor.

The term "BMP4" used herein refers to a protein encoded by the polynucleotide shown in the NCBI Accession Number NM_001202, NM_130850, or NM_130851, and it may be in an active form resulting from cleavage by a protease.

The BMP4 concentration in a culture solution is not particularly limited. For example, such concentration is 10 ng/ml to 1 µg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 µg/ml. The concentration is preferably 20 ng/ml.

While all-trans retinoic acid (ATRA) is exemplified as retinoic acid, artificially modified retinoic acid that retains functions of naturally occurring retinoic acid may be used. Examples thereof include 4-[[(5,6,7,8-tetrahydro-5,5,8,8-tetramethyl-2-naphthalenyl)carbonyl]amino]-benzoic acid (AM580) (Tamura, K. et al., Cell Differ. Dev., 32: 17-26, 1990), 4-R1E)-2-(5,6,7,8-tetrahydro-5,5,8,8-tetramethyl-2-naphthalenyl)-1-propen-1-yl]-benzoic acid (TTNPB) (Strickland, S. et al., Cancer Res., 43: 5268-5272, 1983), retinol palmitate, retinol, retinal, 3-dehydroretinoic acid, 3-dehydroretinol, 3-dehydroretinal, and compounds described in Abe, E. et al., Proc. Natl. Acad. Sci., U.S.A., 78: 4990-4994, 1981; Schwartz, E. L. et al., Proc. Am. Assoc. Cancer Res., 24: 18, 1983; and Tanenaga, K. et al., Cancer Res., 40: 914-919, 1980.

The retinoic acid concentration in a medium is not particularly limited. For example, such concentration is 1 nM to 1 µM, and it is specifically 1 nM, 5 nM, 10 nM, 15 nM, 20 nM, 25 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 µM. The concentration is preferably 50 nM to 1 µM.

The GSK3β inhibitor as described above can be used in this step, and the GSK3β inhibitor is preferably CHIR99021. In this step, the CHIR99021 concentration in a medium is, for example, 1 nM to 50 µM, and it is specifically 1 nM, 10 nM, 50 nM, 100 nM, 500 nM, 750 nM, 1 µM, 1.5 µM, 2 µM, 2.5 µM, 3 µM, 3.5 µM, 4 µM, 4.5 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. In this step, the concentration is preferably 1.5 µM to 3.5 µM.

In this step, culture may be conducted in a culture vessel treated with a coating agent. A coating agent may be a naturally occurring or artificially synthesized extracellular matrix. Examples thereof include BD MATRIGEL®, collagen, gelatin, laminin, heparan sulfate proteoglycan, entactin, and a combination of any thereof, with MATRIGEL® being preferable.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, SOX2-, SOX17-, and/or FOXA2-positive cells may be selected and used in this step. This method is preferably implemented by means of media exchange.

When the step comprises a process of cell detachment, a ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 1 day, 2 days, 3 days, 4 days, 5 days, 6 days, 7 days, or 8 days. The culture period is preferably at least 4 days, and more preferably 4 days.

(4) Step of Ventral Anterior Foregut Cell Culture in a Medium Containing a GSK3β Inhibitor, FGF10, KGF, and a NOTCH Signal Inhibitor (Step 4)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, NEUROBASAL® Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, GLUTAMAX™ (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with GLUTAMAX™, B27 supplement, L-ascorbic acid, monothioglycerol, penicillin, and streptomycin is preferable.

In this step, the ventral anterior foregut cells obtained in the previous step (i.e., the step of culture in a medium containing BMP4, retinoic acid, and a GSK3β inhibitor) are cultured in a medium prepared by supplementing the basal medium with a GSK3β inhibitor, FGF10, KGF, and a NOTCH signal inhibitor.

The GSK3β inhibitor as described above can be used in this step, and the GSK3β inhibitor is preferably CHIR99021. In this step, the CHIR99021 concentration in a medium is, for example, 1 nM to 50 µM, and it is specifically 1 nM, 10 nM, 50 nM, 100 nM, 500 nM, 750 nM, 1 µM, 1.5 µM, 2 µM, 2.5 µM, 3 µM, 3.5 µM, 4 µM, 4.5 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. In this step, the concentration is preferably 3 µM.

The term "FGF10" used herein refers to a protein encoded by the polynucleotide shown in the NCBI Accession Number NM_004465, and it may be in an active form resulting from cleavage by a protease. Such FGF10 is commercially available from, for example, Life Technologies or Wako.

The FGF10 concentration in a medium is not particularly limited. For example, such concentration is 1 ng/ml to 1 µg/ml, and it is specifically 1 ng/ml, 5 ng/ml, 10 ng/ml, 20 ng/ml, 50 ng/ml, 100 ng/ml, 200 ng/ml, 300 ng/ml, 400 ng/ml, 500 ng/ml, or 1 µg/ml. The concentration is preferably 10 ng/ml.

The term "keratinocyte growth factor (KGF)" used herein refers to a protein encoded by the polynucleotide shown in the NCBI Accession Number NM_002009, and it may be in an active form resulting from cleavage by a protease. Such KGF is commercially available from, for example, Wako.

The KGF concentration in a medium is not particularly limited. For example, such concentration is 1 ng/ml to 1 µg/ml, and it is specifically 1 ng/ml, 5 ng/ml, 10 ng/ml, 20 ng/ml, 50 ng/ml, 100 ng/ml, 200 ng/ml, 300 ng/ml, 400 ng/ml, 500 ng/ml, or 1 µg/ml. The concentration is preferably 10 ng/ml.

The term "NOTCH signal inhibitor" used herein refers to a substance that inhibits a Notch signal. Examples thereof include DAPT (N-[2S-(3,5-difluorophenyl)acetyl]-L-alanyl-2-phenyl-1,1-dimethylethyl ester-glycine), DBZ (N-[(1S)-2-[[(7S)-6,7-dihydro-5-methyl-6-oxo-5H-dibenz[b,d]azepin-7-yl]amino]-1-methyl-2-oxoethyl]-3,5-difluorobenzeneacetamide), Compound E (N-[(1S)-2-[[(3S)-2,3-dihydro-1-methyl-2-oxo-5-phenyl-1H-1,4-benzodiazepin-3-yl]-amino]-1-methyl-2-oxoethyl]-3,5-difluorobenzeneacetamide), FLI-06 (cyclohexyl 1,4,5,6,7,8-hexahydro-2,7,7-trimethyl-4-(4-nitrophenyl)-5-oxo-3-quinolinecarboxylate), and LY411575 (N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide).

A NOTCH signal inhibitor that can be preferably used in the present invention is DAPT. The DAPT concentration in a medium is not particularly limited, provided that a Notch signal is inhibited. For example, such concentration is 1 nM to 50 µM, and it is specifically 1 nM, 10 nM, 50 nM, 100 nM, 500 nM, 750 nM, 1 µM, 1.5 µM, 2 µM, 2.5 µM, 3 µM, 3.5 µM, 4 µM, 4.5 µM, 5 µM, 6 µM, 7 µM, 8 µM, 9 µM, 10 µM, 15 µM, 20 µM, 25 µM, 30 µM, 40 µM, or 50 µM, and it is preferably 20 µM.

In this step, culture may be conducted in a culture vessel treated with a coating agent. A coating agent may be a naturally occurring or artificially synthesized extracellular matrix. Examples thereof include BD MATRIGEL®, collagen, gelatin, laminin, heparan sulfate proteoglycan, entactin, and a combination of any thereof, with MATRIGEL® being preferable.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, NKX2-1-, GATA6-, and/or HOPX-positive cells may be selected and used in this step. This method is preferably implemented by means of media exchange.

When the step comprises a process of cell detachment, a ROCK inhibitor may be added to a culture solution, so as to inhibit ventral anterior foregut cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 2 days, 3 days, 4 days, 5 days, 6 days, 7 days, 8 days, 9 days, 10 days, 11 days, 12 days, 13 days, or 14 days. The culture period is preferably at least 7 days, and it is more preferably 7 days.

[Step of Isolating (Selecting) Alveolar Epithelial Progenitor Cells]

The method of the present invention can further comprise, following Step (4), a step of isolating carboxypeptidase M (CPM)-positive cells as alveolar epithelial progenitor cells. The isolated alveolar epithelial progenitor cells can be used in Step (5). The isolated alveolar epithelial progenitor cells may constitute a cell population including alveolar epithelial progenitor cells. Preferably, the alveolar epithelial progenitor cells account for 50%, 60%, 70%, 80%, or 90% or more of the cell population including alveolar epithelial progenitor cells.

Alveolar epithelial progenitor cells can be isolated with the use of reagents having specific affinity to CPM. Examples of reagents having specific affinity that can be used in the present invention include antibodies, aptamers, peptides, and compounds that specifically recognize the substances of interest, with antibodies or fragments thereof being preferable.

Antibodies may be polyclonal or monoclonal antibodies. Examples of antibody fragments include a part of an antibody (e.g., an Fab fragment) and a synthetic antibody fragment (e.g., a single-stranded Fv fragment, ScFv).

In order to recognize or separate cells that express CPM, reagents having relevant affinity may be bound or conjugated to substances that enable detection, such as a fluorescent label, a radioactive label, a chemoluminescent label, an enzyme, biotin, or streptoavidin, or substances that enable isolation and extraction, such as Protein A, Protein G, beads, or magnetic beads.

Alternatively, reagents having relevant affinity may be indirectly labeled. For example, pre-labeled antibodies (secondary antibodies) that specifically bind to the antibodies described above may be used.

Alveolar epithelial progenitor cells can be isolated (extracted) by, for example, a method comprising conjugating particles to a reagent having relevant affinity in order to precipitate the cells, a method involving the use of magnetic beads to select the cells with the aid of magnetism (e.g., MACS), a method involving the use of a cell sorter with the aid of a fluorescent label (e.g., FACS), or a method involving the use of a support upon which antibodies or the like are immobilized (e.g., a cell enrichment column).

[Step of Subjecting Alveolar Epithelial Progenitor Cells to Cryopreservation]

Following Step (4), the resulting alveolar epithelial progenitor cells may be subjected to cryopreservation. Thereafter, the cryopreserved alveolar epithelial progenitor cells may be thawed when Step (5) is initiated.

Alveolar epithelial progenitor cells may be subjected to cryopreservation by, for example, suspending alveolar epithelial progenitor cells in a stock solution comprising dimethyl sulfoxide (DMSO) and the medium for Step (4) at 1:4 to 20 (preferably 1:9), injecting the suspension into a freezing vial, introducing the vial into a cell-freezing container immediately, and freezing the resultant in a deep freezer at −20° C. to −150° C. (preferably at −80° C.) slowly over a period of 4 to 48 hours (preferably 24 hours), followed by storage in a liquid nitrogen tank.

The cryopreserved cells can be thawed by, for example, suspending the cells with the immediate addition of the pre-heated medium used in Step (4), subjecting the same to centrifugation at 300 to 1500 rpm (preferably at 900 rpm) for 1 to 15 minutes (preferably 5 minutes), suction-removing the supernatant, and suspending the resultant again in the medium used in Step (4).

(5) Step of Three-Dimensional Culture of Alveolar Epithelial Progenitor Cells in a Medium Containing a Steroid Drug, a cAMP Derivative, a Phosphodiesterase Inhibitor, and KGF (Step 5)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, NEUROBASAL® Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, ITS Premix, collagen precursors, trace elements, 2-mercaptoethanol, and 3'-thiol glycerol. In addition, a medium can contain one or more substances selected from among, for example, lipids, amino acids, L-glutamine, GLUTAMAX™ (Invitrogen), nonessential amino acids, vitamins, growth factors, low-molecular-weight compounds, antibiotics, antioxidants, pyruvic acids, buffer agents, and inorganic salts. Ham's F12 medium containing BSA, HEPES, calcium chloride, ITS Premix, B27 supplements, penicillin, and streptomycin is preferable.

In this step, the alveolar epithelial progenitor cells obtained in the previous step (i.e., the step of culture in a medium containing a GSK3β inhibitor, FGF10, KGF, and a NOTCH signal inhibitor) are cultured in a medium prepared by supplementing the basal medium with a steroid drug, a cAMP derivative, a phosphodiesterase inhibitor, and KGF.

The term "steroid drug" used herein refers to a steroidal anti-inflammatory drug, such as glucocorticoid or a synthetic derivative thereof. Specific examples thereof include hydrocortisone, hydrocortisone succinate, prednisolone, methylprednisolone, methylprednisolone succinate, triamcinolone, triamcinolone acetonide, dexamethasone, and betamethasone.

A steroid drug that can be preferably used in the present invention is dexamethasone. The dexamethasone concentration in a medium is not particularly limited. For example, such concentration is 1 nM to 1 µM, and it is specifically 1 nM, 5 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 µM. The concentration is preferably 50 nM.

The term "cAMP derivative" used herein refers to a compound with a modified cyclic AMP substituent. Examples thereof include cyclic adenosine monophosphate (cAMP), 8-bromo cyclic adenosine monophosphate (8-Br-cAMP), 8-chloro-cyclic adenosine monophosphate (8-Cl-cAMP), 8-(4-chlorophenylthio)cyclic adenosine monophosphate (8-CPT-cAMP), and dibutyryl cyclic adenosine monophosphate (DB-cAMP).

A cAMP derivative that can be preferably used in the present invention is 8-Br-cAMP. The 8-Br-cAMP concentration in a medium is not particularly limited. For example, such concentration is 1 µM to 1 mM, and it is specifically 1 µM, 5 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, or 1 mM. The concentration is preferably 100 µM.

The term "phosphodiesterase inhibitor" used herein refers to a compound that inhibits phosphodiesterase (PDE), so as to increase the cAMP or cGMP concentration in the cells. Examples thereof include 1,3-dimethylxanthine, 6,7-dimethoxy-1-(3,4-dimethoxybenzyl)isoquinoline, 4-{[3',4'-(methylenedioxy)benzyl]amino}-6-methoxyquinazoline, 8-methoxymethyl-3-isobutyl-1-methylxanthine, and 3-isobutyl-1-methylxanthine (IBMX).

A phosphodiesterase inhibitor that can be preferably used in the present invention is IBMX. The IBMX concentration in a medium is not particularly limited. For example, such concentration is 1 µM to 1 mM, and it is specifically 1 µM, 5 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, or 1 mM. The concentration is preferably 100 µM.

The KGF described above can be used in this step. The KGF concentration in a medium is not particularly limited. For example, such concentration is 10 ng/ml to 1 µg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 µg/ml. The concentration is preferably 10 ng/ml.

In this step, a ROCK inhibitor, such as Y-27632, may further be added to the medium. The Y-27632 concentration in a medium is, for example, 100 nM to 50 µM, and it is specifically 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. The concentration is preferably 10 µM.

In this step, alveolar epithelial progenitor cells are subjected to three-dimensional culture for maturation. The term "three-dimensional culture" used herein refers to float culture of cells in the form of cell masses (i.e., spheroids). Three-dimensional culture can be carried out with the use of, for example, Cell Culture Inserts provided by BD.

Three-dimensional culture may be conducted in the presence of other cell species. Examples of other cell species that may be used include human pulmonary fibroblasts and human fetal pulmonary fibroblasts. Such cells are commercially available from, for example, American Type Culture Collection (ATCC) and DV Biologics. Alveolar epithelial progenitor cells are mixed with other cell species at a rate of, for example, 1:10 to 500, and preferably at 1:50. A cell density in a medium is, for example, $0.5 \times 10^6$ cells to $1 \times 10^7$ cells/ml, and preferably $2.5 \times 10^6$ cells/ml.

The medium used for three-dimensional culture may be prepared with the addition of an extracellular matrix to the medium described above. The ratio of the volume of the medium to the volume of the extracellular matrix is, for example, 1:0.25 to 10, and preferably 1:1. An extracellular matrix is a supramolecular structure that exists outside the cell, and it may be a naturally occurring or artificial (recombinant or peptide hydrogel) structure. Examples thereof include substances, such as collagen, proteoglycan, fibronectin, hyaluronic acid, tenascin, entactin, elastin, fibrillin, and laminin, and fragments thereof. These extracellular matrices may be used in combination. For example, extracellular matrices may be prepared from cells such as Corning MATRIGEL®. An example of an artificial structure is a laminin fragment or Corning PuraMatrix®.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 5 days, 6 days, 7 days, 8 days, 9 days, 10 days, 11 days, 12 days, 13 days, or 14 days. The culture period is preferably at least 14 days, and more preferably 14 days.

[Step of Isolating (Selecting) Type II Alveolar Epithelial Cells]

The method of the present invention can further comprise, following Step (5), a step of isolating type II alveolar epithelial cells. In such step, cells positive for one or more type II alveolar epithelial cell markers selected from the group consisting of SFTPC (surfactant protein C), EpCAM (epithelial cell adhesion molecule), and CEACAM6 (carcinoembryonic antigen-related cell adhesion molecule 6) or cells positive for the type II alveolar epithelial cell markers and staining of acidic fractions (e.g., lysosomes) in live cells with, for example, LysoTracker® may be isolated as type II alveolar epithelial cells.

Type II alveolar epithelial cells can be isolated in accordance with the method for isolating CPM-positive cells as alveolar epithelial progenitor cells. The isolated type II alveolar epithelial cells may constitute a cell population including type II alveolar epithelial cells. Preferably, the type II alveolar epithelial cells account for 5%, 10%, 20%, 30%, 40%, 50%, 60%, 70%, 80%, or 90% or more of the cell population including type II alveolar epithelial cells. [Step of Subjecting Type II Alveolar Epithelial Cells to Cryopreservation]

Following Step (5), the resulting type II alveolar epithelial cells may be subjected to cryopreservation.

Type II alveolar epithelial cells may be subjected to cryopreservation by, for example, suspending type II alveolar epithelial cells in a stock solution comprising DMSO and the medium for Step (5) at 1:4 to 20 (preferably 1:9), injecting the suspension into a freezing vial, introducing the vial into a cell-freezing container immediately, and freezing the resultant in a deep freezer at −20° C. to −150° C. (preferably at −80° C.) slowly over a period of 4 to 48 hours (preferably 24 hours), followed by storage in a liquid nitrogen tank.

The cryopreserved cells can be thawed by, for example, suspending the cells with the immediate addition of the pre-heated medium used in Step (5), subjecting the same to centrifugation at 300 to 1500 rpm (preferably at 900 rpm) for 1 to 15 minutes (preferably 5 minutes), suction-removing the supernatant, and suspending the resultant again in the medium used in Step (5).

[Pluripotent Stem Cells]

Pluripotent stem cells that can be used in the present invention are stem cells that have the potential to differentiate into any types of cells existing in organisms (i.e., pluripotency) and have the potential to grow. Examples thereof include embryonic stem cells (ES cells), nuclear transfer-derived embryonic stem cells from cloned embryos (nt ES cells), sperm stem cells (GS cells), embryonic germ cells (EG cells), induced pluripotent stem cells (iPS cells), and pluripotent cells derived from cultured fibroblasts and myeloid stem cells (Muse cells). In the present invention, the use of iPS cells or Muse cells is preferable because cells of interest can be obtained without destroying embryos.

(A) Embryonic Stem Cells

ES cells are pluripotent stem cells having the potential to grow through autoreproduction, and they are established from embryoblasts of early embryos (e.g., blastocysts) of mammalians such as humans or mice.

ES cells are embryo-derived stem cells originating from embryoblasts of blastocysts, which are embryos after the 8-cell stage and the morula stage of fertilized eggs. Such ES cells have the potential to differentiate into any types of cells constituting an adult; that is, so-called pluripotency, and the potential to grow through autoreproduction. ES cells were discovered in mice in 1981 (M. J. Evans and M. H. Kaufman, 1981, Nature 292: 154-156). Thereafter, ES cells of primates, such as humans and monkeys, were also established (J. A. Thomson et al., 1998, Science 282: 1145-1147; J. A. Thomson et al., 1995, Proc. Natl. Acad. Sci., U.S.A., 92: 7844-7848; J. A. Thomson et al., 1996, Biol. Reprod., 55: 254-259; J. A. Thomson and V. S. Marshall, 1998, Curr. Top. Dev. Biol., 38: 133-165).

ES cells can be established by extracting embryoblasts from blastocysts of fertilized eggs of target animals and culturing the embryoblasts on fibroblast feeders. Cells can be maintained via subculture with the use of a culture solution supplemented with substances such as leukemia inhibitory factors (LIF) and basic fibroblast growth factors (bFGF). Human and monkey ES cells can be established and maintained by the methods described in, for example, U.S. Pat. No. 5,843,780; Thomson J. A. et al., 1995, Proc. Natl. Acad. Sci., U.S.A., 92: 7844-7848; Thomson, J. A. et al., 1998, Science 282: 1145-1147; H. Suemori et al., 2006, Biochem. Biophys. Res. Commun., 345: 926-932; M. Ueno et al., 2006, Proc. Natl. Acad. Sci. U.S.A., 103: 9554-9559; H. Suemori et al., 2001, Dev. Dyn., 222: 273-279; H. Kawasaki et al., 2002, Proc. Natl. Acad. Sci. U.S.A., 99: 1580-1585; and Klimanskaya I et al., 2006, Nature 444: 481-485.

Human ES cells can be maintained with the use of a medium for ES cell production, such as a DMEM/F-12 medium supplemented with 0.1 mM 2-mercaptoethanol, 0.1 mM nonessential amino acids, 2 mM L-glutamic acid, 20% KSR, and 4 ng/ml bFGF, at 37° C. in the presence of 5% $CO_2$ in a moist atmosphere (H. Suemori et al., 2006, Biochem. Biophys. Res. Commun., 345: 926-932). It is necessary that ES cells be subjected to subculture every 3 or 4 days. Subculture can be carried out with the use of, for example, 0.25% trypsin and 0.1 mg/ml collagenase IV in PBS containing 1 mM $CaCl_2$ and 20% KSR.

In general, ES cells can be selected via real-time PCR using the expression of a gene marker such as alkaline phosphatase, Oct-3/4, or Nanog as an indicator. When human ES cells are to be selected, in particular, the expression of a gene marker such as OCT-3/4, NANOG, or ECAD can be employed as an indicator (E. Kroon et al., 2008, Nat. Biotechnol., 26: 443-452).

Human ES cells (e.g., WA01 (H1) and WA09 (H9)) are available from the WiCell Research Institute, and KhES-1, KhES-2, and KhES-3 are available from the Institute for Frontier Medical Sciences, Kyoto University (Kyoto, Japan).

(B) Sperm Stem Cells

Sperm stem cells are testis-derived pluripotent stem cells that serve as sources for spermatogenesis. As with the case of ES cells, sperm stem cells can be differentiated into various types of cells. For example, sperm stem cells may be implanted into mouse blastocysts, so that chimeric mice may be produced (M. Kanatsu-Shinohara et al., 2003, Biol. Reprod., 69: 12-616; K. Shinohara et al., 2004, Cell, 119: 1001-1012). Sperm stem cells are capable of autoreproduction in a medium containing glial cell line-derived neurotrophic factors (GDNF). In addition, sperm stem cells can be obtained by repeating subculture under the same culture conditions as with those used for ES cells (Masanori Takebayashi et al., 2008, Experimental Medicine, Vol. 26, No. 5 (extra edition), pp. 41-46, Yodosha, Tokyo, Japan).

(C) Embryonic Germ Cells

As with ES cells, embryonic germ cells are pluripotent cells that are established from primordial germ cells during the prenatal period. Embryonic germ cells can be established by culturing primordial germ cells in the presence of substances such as LIF, bFGF, or stem cell factors (Y. Matsui et al., 1992, Cell, 70: 841-847; J. L. Resnick et al., 1992, Nature, 359: 550-551).

(D) Induced Pluripotent Stem Cells

Induced pluripotent stem (iPS) cells can be prepared by introducing particular reprogramming factors into somatic cells in the form of DNA or proteins. iPS cells are artificial stem cells derived from somatic cells that have substantially the same properties as ES cells, such as pluripotency and the potential to grow through autoreproduction (K. Takahashi and S. Yamanaka, 2006, Cell, 126: 663-676; K. Takahashi et al., 2007, Cell, 131: 861-872; J. Yu et al., 2007, Science, 318: 1917-1920; Nakagawa, M. et al., Nat. Biotechnol., 26: 101-106, 2008; WO 2007/069666). Reprogramming factors may be composed of genes that are expressed specifically in ES cells, gene products or non-cording RNA thereof, genes that play key roles in maintenance of the undifferentiated state of ES cells, gene products or non-coding RNA thereof, or low-molecular-weight compounds. Examples of genes included in reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. Such reprogramming factors may be used alone or in combination. Examples of combinations of reprogramming factors are described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu, D. et al., 2008, Nat. Biotechnol., 26: 795-797, Shi, Y. et al., 2008, Cell Stem Cell, 2: 525-528, Eminli, S. et al., 2008, Stem Cells, 26: 2467-2474, Huangfu, D. et al., 2008, Nat. Biotechnol., 26: 1269-1275, Shi, Y. et al., 2008, Cell Stem Cell, 3, 568-574, Zhao, Y. et al., 2008, Cell Stem Cell, 3: 475-479, Marson, A. 2008, Cell Stem Cell, 3, 132-135, Feng, B. et al., 2009, Nat Cell Biol., 11: 197-203, R. L. Judson et al., 2009, Nat. Biotech., 27: 459-461, Lyssiotis, C. A. et al., 2009, Proc. Natl. Acad. Sci., U.S.A. 106: 8912-8917, Kim, J. B. et al., 2009, Nature, 461: 649-643, Ichida, J. K. et al., 2009, Cell Stem Cell, 5: 491-503, Heng, J. C. et al., 2010, Cell Stem Cell, 6: 167-74, Han, J. et al., 2010, Nature, 463: 1096-100, Mali, P. et al., 2010, and Stem Cells, 28: 713-720, Maekawa, M. et al., 2011, Nature, 474: 225-9.

Factors that are used to enhance cell establishment efficiency are within the scope of the reprogramming factors described above. Examples thereof include: histone deacetylase (HDAC) inhibitors, such as low-molecular-weight inhibitors, including valproic acid (VPA), trichostatin A, sodium butyrate, MC 1293, and M344, and nucleic acid-based expression inhibitors, including siRNAs and shRNAs against HDAC (e.g., HDAC1 siRNA Smartpool® (Millipore) and HuSH 29mer shRNA constructs against HDAC1 (OriGene)); MEK inhibitors (e.g., PD184352, PD98059, U0126, SL327, and PD0325901); glycogen synthase kinase-3 inhibitors (e.g., Bio and CHIR99021); DNA methyltransferase inhibitors (e.g., 5-azacytidine); histone methyltransferase inhibitors (e.g., low-molecular-weight inhibitors, such as BIX-01294, and nucleic acid-based expression inhibitors against Suv39h1, Suv39h2, SetDB1 and G9a, such as siRNAs and shRNAs); an L-channel calcium agonist (e.g., Bayk8644); butyric acid, TGFβ inhibitor, and ALK5 inhibitor (e.g., LY364947, SB431542, 616453, and A-83-01); p53 inhibitors (e.g., siRNA and shRNA against p53); ARID3A inhibitors (e.g., siRNA and shRNA against ARID3A), miRNA, such as miR-291-3p, miR-294, miR-295, and mir-302, Wnt signaling (e.g., soluble Wnt3a), neuro-peptide Y, prostaglandins (e.g., prostaglandin E2 and prostaglandin J2), hTERT, SV40LT, UTF1, IRX6, GLIS1, PITX2, and DMRTB1. Such factors used to enhance cell establishment efficiency are not particularly distinguished from reprogramming factors herein.

When reprogramming factors are in the form of proteins, for example, they may be introduced into somatic cells by a technique such as lipofection, fusion with cell-permeable peptides (e.g., HIV-derived TAT and polyarginine), or microinjection.

In contrast, reprogramming factors in the form of DNA can be introduced into somatic cells by a technique involving the use of a vector such as a virus, plasmid, or artificial chromosome vector, lipofection, a technique involving the use of a liposome, or microinjection, for example. Examples of virus vectors include retrovirus vectors, lentivirus vectors (Cell, 126, pp. 663-676, 2006; Cell, 131, pp. 861-872, 2007; Science, 318, pp. 1917-1920, 2007), adenovirus vectors (Science, 322, 945-949, 2008), adeno-associated virus vectors, and Sendai virus vectors (WO 2010/008054). Examples of artificial chromosome vectors include human artificial chromosome (HAC) vectors, yeast artificial chromosome (YAC) vectors, and bacterial artificial chromosome (BAC, PAC) vectors. Plasmids for mammalian animal cells can be used (Science, 322: 949-953, 2008). Vectors can comprise regulatory sequences, such as promoters, enhancers, ribosome-binding sequences, terminators, or polyadenylation sites, so that nuclear reprogramming substances can express. In addition, vectors can comprise selection marker sequences, such as drug tolerance genes (e.g., kanamycin tolerance genes, ampicillin tolerance genes, and puromycin tolerance genes), thymidine kinase genes, or diphtheria toxin genes, and reporter gene sequences, such as green fluorescent proteins (GFP), β-glucuronidase (GUS), or FLAG, according to need. The vector may comprise LoxP sequences in positions downstream and upstream of a gene encoding a reprogramming factor or a gene encoding a promoter and a reprogramming factor binding thereto, so as to eliminate such gene after the vector is introduced into somatic cells.

When reprogramming factors are in the form of RNA, for example, they may be introduced into somatic cells by a technique such as lipofection or microinjection. Alternatively, RNA comprising 5-methylcytidine and pseudouridine (TriLink Biotechnologies) incorporated therein may be used, so as to suppress degradation (Warren L, 2010, Cell Stem Cell 7: 618-630).

Examples of culture media used for iPS cell induction include DMEM containing 10% to 15% FBS, a DMEM/F12 or DME medium (such medium may adequately contain, for example, LIF, penicillin/streptomycin, puromycin, L-glutamine, nonessential amino acids, and β-mercaptoethanol), commercially available culture media (e.g., a medium for mouse ES cell culture; TX-WES medium, Thrombo X), a medium for primate ES cell culture (a medium for primate ES/iPS cell culture, ReproCELL Incorporated), and a serum-free medium (mTeSR, Stemcell Technology).

For example, somatic cells are brought into contact with reprogramming factors in a 10% FBS-containing DMEM or DMEM/F12 medium, culture is conducted at 37° C. in the presence of 5% $CO_2$ for about 4 to 7 days, and the cells are reseeded on feeder cells (e.g., mitomycin C-treated STO cells or SNL cells). Culture is reinitiated in a medium for bFGF-containing primate ES cell culture about 10 days after the somatic cells are first brought into contact with the reprogramming factors, and iPS-like colonies can then be formed at least about 30 to 45 days after such contact.

Alternatively, culture may be conducted in a 10% FBS-containing DMEM medium (this medium can further contain LIF, penicillin/streptomycin, puromycin, L-glutamine, nonessential amino acids, β-mercaptoethanol, or the like, according to need) on feeder cells (e.g., mitomycin C-treated STO cells or SNL cells) at 37° C. in the presence of 5% $CO_2$, and ES-like colonies can then be formed at least about 25 to 30 days later. Alternatively, use of the somatic cells to be reprogrammed instead of feeder cells is preferable (Takahashi K, et al., 2009, PLoS One, 4: e8067 or WO 2010/137746), or use of an extracellular matrix (e.g., laminin-5 (WO 2009/123349) and Matrigel (BD)) is preferable.

In addition, culture may be conducted with the use of a serum-free medium (Sun, N. et al., 2009, Proc. Natl. Acad. Sci., U.S.A. 106: 15720-15725). In order to enhance cell establishment efficiency, iPS cells may be established under low-oxygen conditions (oxygen concentration of 0.1% to 15%) (Yoshida, Y. et al., 2009, Cell Stem Cell, 5: 237-241 or WO 2010/013845).

During the culture, medium exchange is initiated 2 days after the initiation of culture, and the medium is exchanged with a fresh medium once a day. The number of somatic cells used for nuclear reprogramming is not limited, and it is about $5 \times 10^3$ to about $5 \times 10^6$ cells per 100 $cm^2$ of a culture dish.

iPS cells can be selected in accordance with the configuration of the formed colonies. When drug tolerance genes that express in association with genes that express upon reprogramming of somatic cells (e.g., Oct3/4 and Nanog) are introduced as marker genes, in contrast, culture can be conducted in a medium containing corresponding drugs (i.e., a selection medium). Thus, established iPS cells can be selected. When marker genes are fluorescent protein genes, fluorescent microscopic observation may be carried out. When marker genes are luminescent enzyme genes, luminescent substrates may be added. When marker genes are chromogenic enzyme genes, chromogenic substrates may be added. Thus, iPS cells can be selected.

The term "somatic cells" used herein refers to any animal cells except for germline cells or pluripotent cells such as egg cells, oocytes, and ES cells (preferably mammalian animal cells, including those of humans). Examples of somatic cells include, but are not limited to, embryonic (fetal) somatic cells, neonatal (fetal) somatic cells, and mature healthy or affected somatic cells. Somatic cells may be primary-cultured cells, subcultured cells, or established cells. Specific examples of somatic cells include: (1) tissue stem cells, such as neural stem cells, hematopoietic stem cells, mesenchymal stem cells, and dental pulp stem cells (i.e., somatic stem cells); (2) tissue progenitor cells; and (3) differentiated cells, such as lymphocytes, epidermic cells, endothelial cells, muscle cells, fibroblasts (e.g., skin cells), hair cells, hepatic cells, gastric mucosal cells, intestinal cells, splenic cells, pancreatic cells (e.g., pancreatic exocrine cells), brain cells, pneumocytes, nephrocytes, and adipocytes.

When iPS cells are used as materials for transplantation, use of somatic cells having the same or substantially the same HLA genotype as that of a recipient is preferable, so that rejection would not occur. When HLA genotypes are "substantially the same," such HLA genotypes are concordant with each other to the extent that an immunosuppressive agent is able to suppress immune responses to the transplanted cells. For example, such somatic cells have HLA genotypes exhibiting concordance in 3 loci; i.e., HLA-A, HLA-B, and HLA-DR, or in 4 loci; i.e., HLA-A, HLA-B, HLA-DR, and HLA-C.

(E) Nuclear Transfer-Derived ES Cells from Cloned Embryos

"nt ES cells" are nuclear transfer-derived ES cells produced from cloned embryos, and such ES cells have substantially the same properties as fertilized egg-derived ES cells (T. Wakayama et al., 2001, Science, 292: 740-743; S. Wakayama et al., 2005, Biol. Reprod., 72: 932-936; J. Byrne et al., 2007, Nature, 450: 497-502). Specifically, nuclear transfer ES cells (i.e., nt ES cells) are ES cells that are established from embryoblasts of blastocysts derived from cloned embryos resulting from substitution of an unfertilized egg nucleus with a somatic cell nucleus. nt ES cells are produced by the technique of nuclear transfer (J. B. Cibelli et al., 1998, Nature Biotechnol., 16: 642-646) in combination with the technique of ES cell production (Kiyoka Wakayama et al., 2008, Experimental Medicine, Vol. 25, No. 5 (extra edition), pp. 47-52). In the case of nuclear transfer, somatic cell nuclei are injected into enucleated unfertilized eggs of mammalian animals, and culture is conducted for several hours. Thus, such cells can be reprogrammed.

(F) Multilineage-Differentiating Stress Enduring Cells (Muse Cells)

Muse cells are pluripotent stem cells produced by the method described in WO 2011/007900. More specifically, Muse cells are pluripotent cells that are obtained by treating fibroblasts or myeloid interstitial cells with trypsin for a long period of time (preferably for 8 hours or 16 hours) and conducting float culture. Such cells are positive for SSEA-3 and CD105.

[Kit for Producing Type II Alveolar Epithelial Cells from Pluripotent Stem Cells]

The present invention provides a kit for producing type II alveolar epithelial cells from pluripotent stem cells. The kit may comprise growth factors, compounds, a medium, extracellular matrices, a cell detachment solution, and an agent for coating the culture vessel as used for induction of differentiation. The kit may further comprise documents and/or instructions describing the procedure for the induction of differentiation.

[Method for Type II Alveolar Epithelial Cell Culture]

In accordance with Step (5) of the method for producing type II alveolar epithelial cells from pluripotent stem cells according to the present invention, the present invention relates to a method for type II alveolar epithelial cell culture comprising a step of three-dimensional culture of type II alveolar epithelial cells in a medium containing a steroid drug, a cAMP derivative, a phosphodiesterase inhibitor, and KGF. An ROCK inhibitor, such as Y-27632, may further be added to the medium.

With the addition of the WNT signal inhibitor and/or IGF2 to the medium, type II alveolar epithelial cells can be maintained efficiently.

The term "WNT signal inhibitor" refers to a substance that inhibits WNT signals. Examples thereof include protein inhibitors, such as WIF1, and low-molecular-weight compounds, such as IWP2 (N-(6-methyl-2-benzothiazolyl)-2-[(3,4,6,7-tetrahydro-4-oxo-3-phenylthieno[3,2-d]pyrimidin-2-yl)thio]-acetamide), IWR1 (4-(1,3,3a,4,7,7a-hexahydro-1,3-dioxo-4,7-methano-2H-isoindol-2-yl)-N-8-quinolinyl-benzamide), and ICG-001 ((6S,9aS)-hexahydro-6-[(4-hydroxyphenyl)methyl]-8-(1-naphthalenylmethyl)-4,7-dioxo-N-(phenylmethyl)-2H-pyrazino[1,2-a]pyrimidine-1 (6H)-carboxamide).

The term "WIF1" used herein refers to a protein encoded by the polynucleotide shown in the NCBI Accession Number NM_007191, and it may be in an active form resulting from cleavage by a protease. Such WIF1 is commercially available from, for example, R&D Systems.

The term "IGF2" used herein refers to a protein encoded by the polynucleotide shown in the NCBI Accession Number NM_000612, and it may be in an active form resulting from cleavage by a protease. Such IGF2 is commercially available from, for example, R&D Systems and Life Technologies.

A WNT signal inhibitor that can be preferably used in the present invention is WIF1.

The WIF1 concentration in a medium is, for example, 10 ng/ml to 1 μg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 μg/ml, although the concentration is not limited thereto. The concentration is preferably 300 ng/ml.

The IGF2 concentration in a medium is, for example, 10 ng/ml to 1 μg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 μg/ml, although the concentration is not limited thereto. The concentration is preferably 100 ng/ml.

Type II alveolar epithelial cells may be primary-cultured cells isolated from, for example, tissue, or type II alveolar epithelial cells may be produced by the method for producing type II alveolar epithelial cells from pluripotent stem cells according to the present invention.

The process of subculture carried out in this step can be repeated at intervals of, for example, at least 14 days to 35 days, specifically, at intervals of at least 14 days, 16 days, 18 days, 20 days, 21 days, 22 days, 24 days, 26 days, 28 days, 30 days, 32 days, 34 days, or 35 days, and, preferably, at intervals of 14 days.

[Kit for Type II Alveolar Epithelial Cell Culture]

The present invention provides a kit for type II alveolar epithelial cell culture. The kit may comprise growth factors, compounds, a medium, an extracellular matrix, a cell detachment solution, and an agent for coating the culture vessel used for the culture described above. The kit may further comprise documents and/or instructions describing the procedure for the culture.

[Applications of Type II Alveolar Epithelial Cells Obtained in the Present Invention]

The type II alveolar epithelial cells obtained in the present invention can be used for large-scale screening of candidate drugs in vitro when developing therapeutic agents for intractable respiratory diseases, such as idiopathic pulmonary fibrosis, hereditary interstitial lung disease, and congenital pulmonary alveolar proteinosis.

The type II alveolar epithelial cells obtained in the present invention can be administered to patients afflicted with diseases that destroy the pulmonary alveolus in the form of pharmaceutical preparations. The type II alveolar epithelial cells are prepared into the form of a sheet, and the sheet may be applied to the alveolar epithelium of a patient. Alternatively, the type II alveolar epithelial cells may be suspended in physiological saline or the like, and the suspension may then be directly implanted in the pulmonary alveolus of the patient. Accordingly, the present invention provides an agent for treatment of pulmonary alveolar diseases comprising type II alveolar epithelial cells obtained from pluripotent stem cells in the manner described above.

In the present invention, the number of type II alveolar epithelial cells contained in the agent for treatment of pulmonary alveolar diseases is not particularly limited, provided that the transplanted grafts are able to survive after their administration. The number of the cells may be adequately adjusted in accordance with lesion size or body size.

Hereafter, the present invention is described in greater detail with reference to the Examples, although the technical scope of the present invention is not limited to these Examples.

[Example 1] Method for Inducing Type II Alveolar Epithelial Cells

1. Method for Inducing Type II Alveolar Epithelial Cells

FIG. 1 shows a method for inducing type II alveolar epithelial cells from ventral anterior foregut cells using human pluripotent stem cells.

1-1. Induction of Differentiation from Human Pluripotent Stem Cells into Ventral Anterior Foregut Cells in Step 1-3

In accordance with the method described in Gotoh, S. et al., Stem Cell Reports, 2014, Vol. 3, pp. 394-403, human pluripotent stem cells were induced to differentiate into ventral anterior foregut cells.

Human iPS cells (201B7, 604A1) were provided by Professor Yamanaka at Kyoto University, human ES cells (H9) were provided by WiCell Research Institute, and the cells were cultured in accordance with a conventional technique (Takahashi, K. et al., Cell, 131: 861-872, 2007; Okita, K., et al., Stem Cells, 31: 458-466, 2013; Gotoh, S., et al., Stem Cell Reports, 3: 394-403, 2014).

In accordance with the method described in Mae S., et al, Nat. Commun., 4: 1367, 2013, according to a gene knock-in technique, SFTPC-reporter 201B7 (i.e., (SFTPC-GFP reporter iPS cell line B2-3) was produced by introducing an EGFP sequence into a site downstream of the SFTPC initiation codon of the human iPS cells (201B7).

The ventral anterior foregut cells were induced by detaching human pluripotent stem cells with the use of Accutase, seeding the cells in a 24-well plate coated with Matrigel at $2.0 \times 10^5$ cells/well or in a 6-well plate coated with Matrigel at $9.6 \times 10^5$ cells/well, and conducting culture under the conditions described below.

1-1-1. Step 1

The seeded cells (Day 0) were cultured in a basal medium (RPMI1640 (Nacalai Tesque) containing 2% B27 (Life Technologies) and a 0.5% penicillin/streptomycin stock solution (Life Technologies)) supplemented with 100 ng/ml activin A (R&D Systems), 1 μM CHIR99021, and 10 μM Y-27632. On the following day (Day 1), the medium was exchanged with the basal medium containing 100 ng/ml activin A, 1 μM CHIR99021, and 0.25 mM NaB, the medium was exchanged with another medium under the same conditions on the following day (Day 2) and 3 days later (Day 4), and culture was conducted for 5 days.

Alternatively, the seeded cells (Day 0) were cultured in the basal medium supplemented with 100 ng/ml activin A, 1 μM CHIR99021, and 10 μM Y-27632. On the following day (Day 1), the medium was exchanged with the basal medium containing 100 ng/ml activin A, 1 μM CHIR99021, 10 μM Y-27632, and 0.125 mM or 0.25 mM NaB. On the following day (Day 2), the medium was exchanged with the basal medium containing 100 ng/ml activin A, 1 μM CHIR99021, and 0.125 mM or 0.25 mM NaB. The medium was then exchanged with another medium of the same conditions 3 days after the initiation of culture (Day 4).

1-1-2. Step 2

The cells obtained in Step 1 (Day 6) were cultured in a basal medium (DMEM/F12 medium (Life Technologies) containing 1% GLUTAMAX™ supplement (Life Technologies), 2% B27 supplement, 1% N2 supplement (Life Technologies), 0.8% StemSure™ 50 mmol/l monothioglycerol solution (Wako), 50 μg/ml L-ascorbic acid (Sigma Aldrich), and 0.5% penicillin/streptomycin stock solution) supplemented with 100 ng/ml hNoggin (R&D Systems) and 10 μM SB-431542 for 4 days. In this case, the medium was exchanged with another medium under the same conditions every other day.

1-1-3. Step 3

The cells obtained in Step 2 (Day 10) were cultured in the basal medium used in Step 2 containing 20 ng/ml hBMP4 (HumanZyme, Inc.), 0.05 μM, 0.5 μM, or 1.0 μM all-trans retinoic acid (ATRA), and 2.5 μM or 3.5 μM CHIR99021 for 4 days. In this case, the medium was exchanged with another medium under the same conditions every other day.

1-2. Two-Dimensional Culture in Step 4

The ventral anterior foregut cells on Day 14 (upon completion of Step 3) induced to differentiate in Section 1-1 above were cultured in the medium for Step 4 for 7 days and the alveolar epithelial progenitor cells were thus obtained efficiently. The composition of the medium for Step 4 was composed of a basal medium comprising DMEM/F12 (Life Technologies), lx GLUTAMAX™ (Life Technologies), lx B27 supplement (Life Technologies), 0.05 mg/ml L-ascorbic acid (Sigma-Aldrich), 0.4 mM monothioglycerol (Wako), and 50 U/ml penicillin/streptomycin (Life Technologies) supplemented with 3 μM CHIR99021, 10 ng/ml FGF10, 10 ng/ml KGF (Prospec), and 20 μM DAPT.

1-3. Isolation of Alveolar Epithelial Progenitor Cells Via FACS

On Day 21 (upon completion of Step 4) in Section 1-2 above, the alveolar epithelial progenitor cells were isolated with the use of antibodies reacting with CPM via fluorescence activated cell sorting (FACS). Y-27632 (10 μM) was added to the medium 1 hour before the alveolar epithelial progenitor cells were peeled. Thereafter, the culture plate was washed with PBS (Nacalai Tesque), and 0.5 mM EDTA/PBS was added, followed by incubation at 37° C. for 12 minutes. After EDTA/PBS was removed, Accutase (Innovative Cell Technologies) was added, incubation was carried out at 37° C. for 25 minutes, a DMEM medium (Nacalai Tesque) supplemented with 2% FBS (Life Technologies) was added, and the cells were then recovered via pipetting. The recovered cell suspension was allowed to pass through a 40 μm cell strainer mesh (BD Falcon), and the resultant was centrifuged at 800 rpm for 5 minutes, followed by washing with 1% BSA/PBS. The mouse anti-human CPM antibody (Leica Microsystems) was added as the primary antibody, and the reaction was then allowed to proceed at 4° C. for 15 minutes.

After the completion of primary antibody treatment, the cells were washed 2 times with 1% BSA/PBS, the ALEXA FLUOR® 647-labeled anti-mouse IgG antibody (Life Technologies) was added as the secondary antibody, and the reaction was then allowed to proceed in the dark at 4° C. for 15 minutes. After the completion of secondary antibody treatment, the cells were washed 2 times with 1% BSA/PBS, and propidium iodide was added in the end. Thereafter, CPM-positive cells and CPM-negative cells were isolated via FACS with the use of BD FACSAria® II or FacsAria® III (BD Biosciences), and the CPM-positive cells were used as the alveolar epithelial progenitor cells. As the isotype control, cells treated with mouse IgG1 (Sigma-Aldrich) were used for FACS gating.

1-4. Three-Dimensional Coculture in Step 5

The alveolar epithelial progenitor cells isolated via FACS or MACS in Step 4 or the cryopreserved alveolar epithelial progenitor cells were mixed with the human fetal lung fibroblasts (17.5-weeks pregnant, DV Biologies) at a ratio of 2:100, the cell suspension comprising the cells at a cell density of $2.5 \times 10^6$ cells/ml and the medium for Step 5 supplemented with Y-27632 at the final concentration of 10 μM was mixed with MATRIGEL® (Corning) at a ratio of 1:1 at a low temperature, the resultant was immediately added to the upper layer of the Cell Culture Inserts, and the medium for Step 5 was added to the lower layer. At this time, the amount to be added to the upper layer of the 12-well plate Cell Culture Inserts is preferably 200 to 400 μL and the amount to be added to the upper layer of the 24-well plate Cell Culture Inserts is preferably 100 μl. The amount of the medium for Step 5 to be added to the lower layer of the 12-well plate Cell Culture Inserts is preferably 1 ml, and the amount thereof to be added to the lower layer of the 24-well plate Cell Culture Inserts is preferably 500 μl.

On the first 2 days, Y-27632 was added to the medium for Step 5 to the final concentration of 10 μM. Thereafter, the medium for Step 5 of the lower layer was selectively exchanged with another medium every other day.

The medium for Step 5 was prepared with the addition of 50 nM dexamethasone (Sigma-Aldrich), 100 μM 8-Br-cAMP (Biolog), 100 μM IBMX (Wako), and 10 ng/ml KGF (Prospec) to the basal medium composed of Hams' F12 (Wako), 0.25% BSA (Life Technologies), 15 mM HEPES (Sigma-Aldrich), 0.8 mM $CaCl_2$) (Nacalai Tesque), 1x ITS Premix (Corning), 0.5x B27 Supplement (Life Technologies), and 50 U/ml penicillin/streptomycin (Life Technologies).

2. Results of Induction of Type II Alveolar Epithelial Cells

FIG. 2 shows the results of examination of the composition of the medium for Step 4 shown in FIG. 1 in terms of the efficiency for alveolar epithelial progenitor cell induction and isolation using NKX2.1 as a marker protein.

FIG. 2A to FIG. 2D demonstrate as follows.

Figures 2A, 2B:
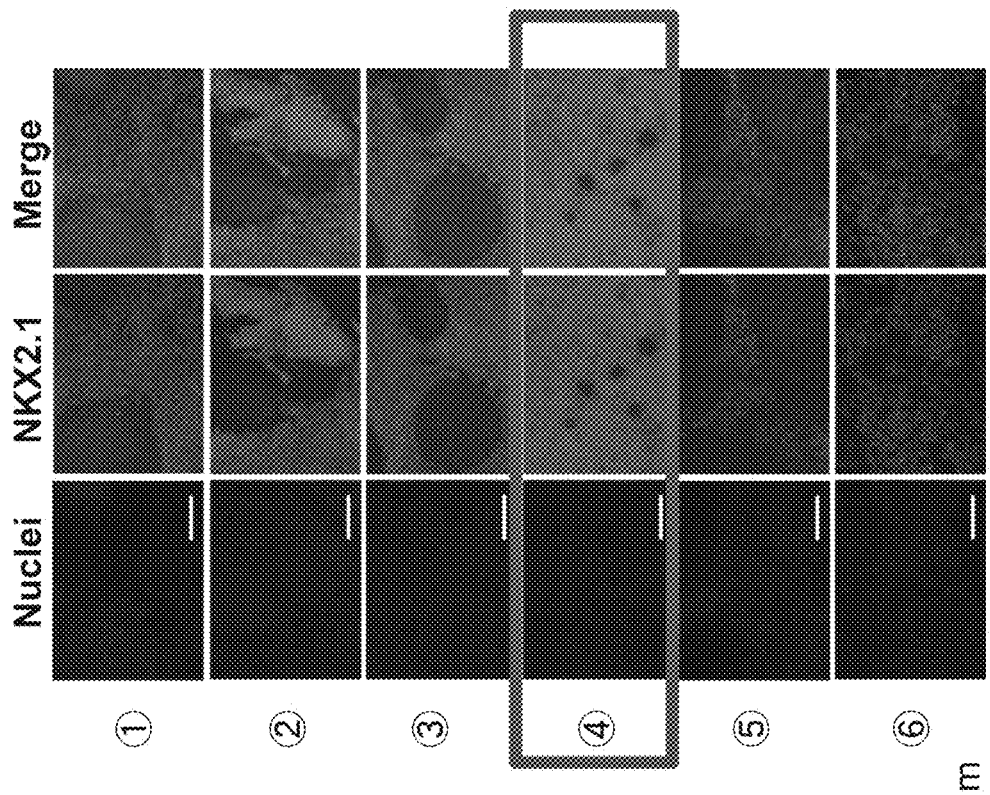
FIGS. 2A and 2B show the results of examination of the composition of the medium for Step 4 shown in FIG. 1 in terms of the efficiency for alveolar epithelial progenitor cell induction and isolation using NKX2.1 as a marker protein.

FIG. 2A shows 6 conditions under which examinations were carried out.

FIG. 2B shows fluorescent immunostaining images of NKX2.1$^+$ cells on Day 21 (i.e., upon completion of Step 4) after ventral anterior foregut cells were cultured under each condition for 7 days. The highest NKX2.1-positive rate was achieved under the condition (4).

FIG. 2C shows the results of flow cytometry of alveolar epithelial progenitor cells cultured under the condition (4) on Day 21 (i.e., upon completion of Step 4) with the use of the anti-CPM antibody. The results indicate that the human iPS cell lines (201B7, 604A1) and the human ES cell line (H9) contain large quantities of CPM cells.

FIG. 2D shows the results of nuclear staining of CPM cells and CPM$^-$ cells isolated from the cell lines shown in FIG. 2C and allowed to adhere to glass slides via cytospinning and fluorescent immunostaining of NKX2.1 carried out simultaneously therewith. The results demonstrate that most NKX2.1$^+$ cells are included in CPM cells and NKX2.1$^-$ cells are not substantially included in CPM$^-$ cells. While the case of the ventral anterior foregut cells on Day 14 (i.e., upon completion of Step 3) was described in Gotoh, S. et al., Stem Cell Reports, 2014, Vol. 3, pp. 394-403, it was confirmed that the same would apply to the case on Day 21 (i.e., upon completion of Step 4).

Figure 3:
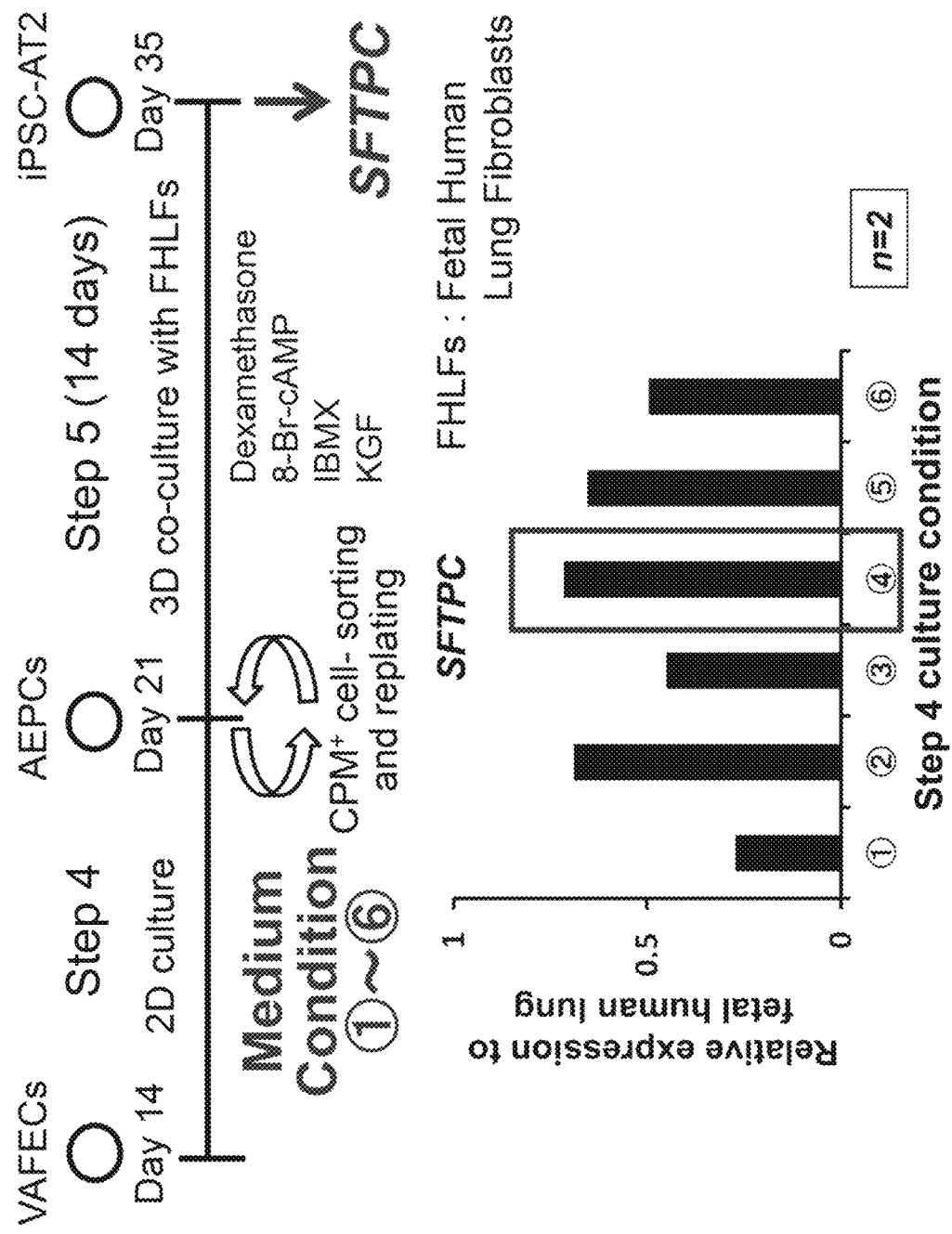
FIG. 3 shows the results of examination of the composition of the medium for Step 4 in terms of the expression level of SFTPC, which is a marker protein for type II alveolar epithelial cells, on Day 35 (i.e., upon completion of Step 5).

FIG. 3 shows the results of examination of the composition of the medium for Step 4 in terms of the expression level of SFTPC, which is a marker protein for type II alveolar epithelial cells, on Day 35 (i.e., upon completion of Step 5). The ventral anterior foregut cells were cultured in the media under the 6 different conditions shown in FIG. 2 for 7 days, CPM$^+$ cells were isolated on Day 21 (i.e., upon completion of Step 4), the cells were subjected to three-dimensional coculture with human fetal lung fibroblasts for 14 days, and the SFTPC expression levels were then evaluated via quantitative RT-PCR on Day 35 (i.e., upon completion of Step 5). The highest SFTPC expression level was observed under the condition (4) among the 6 conditions.

Figure 4:
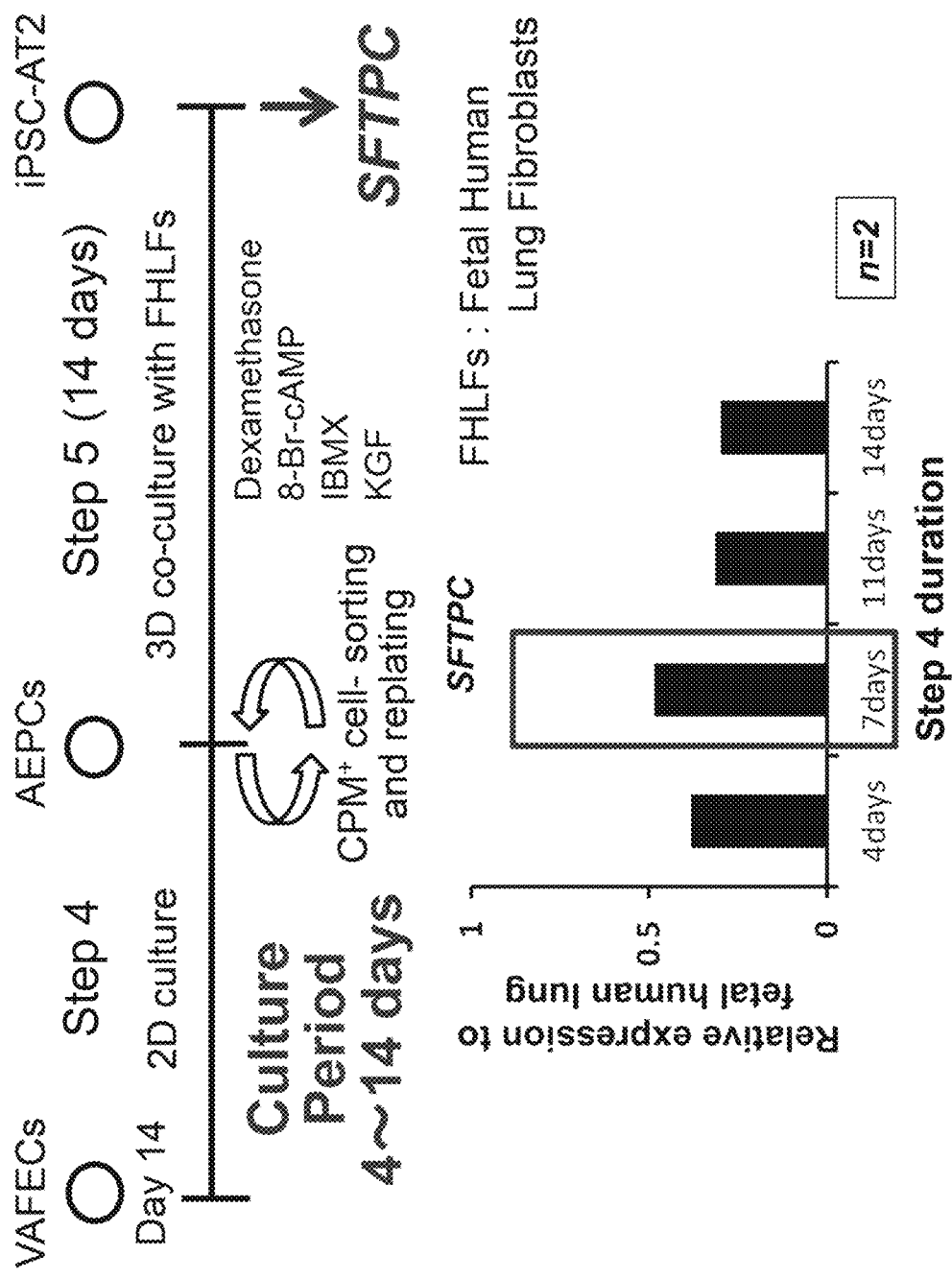
FIG. 4 shows the results of examination of the culture period under the conditions shown in FIG. 2 (4) in terms of the expression level of SFTPC, which is a marker protein for type II alveolar epithelial cells, on Day 35 (i.e., upon completion of Step 5).

FIG. 4 shows the results of examination of the culture period under the conditions shown in FIG. 2 (4) in terms of the expression level of SFTPC, which is a marker protein for type II alveolar epithelial cells, on Day 35 (i.e., upon completion of Step 5). The results indicate that the SFTPC expression level was likely to be high on Day 35 when the duration of Step 4 is 7 days.

Figure 5:
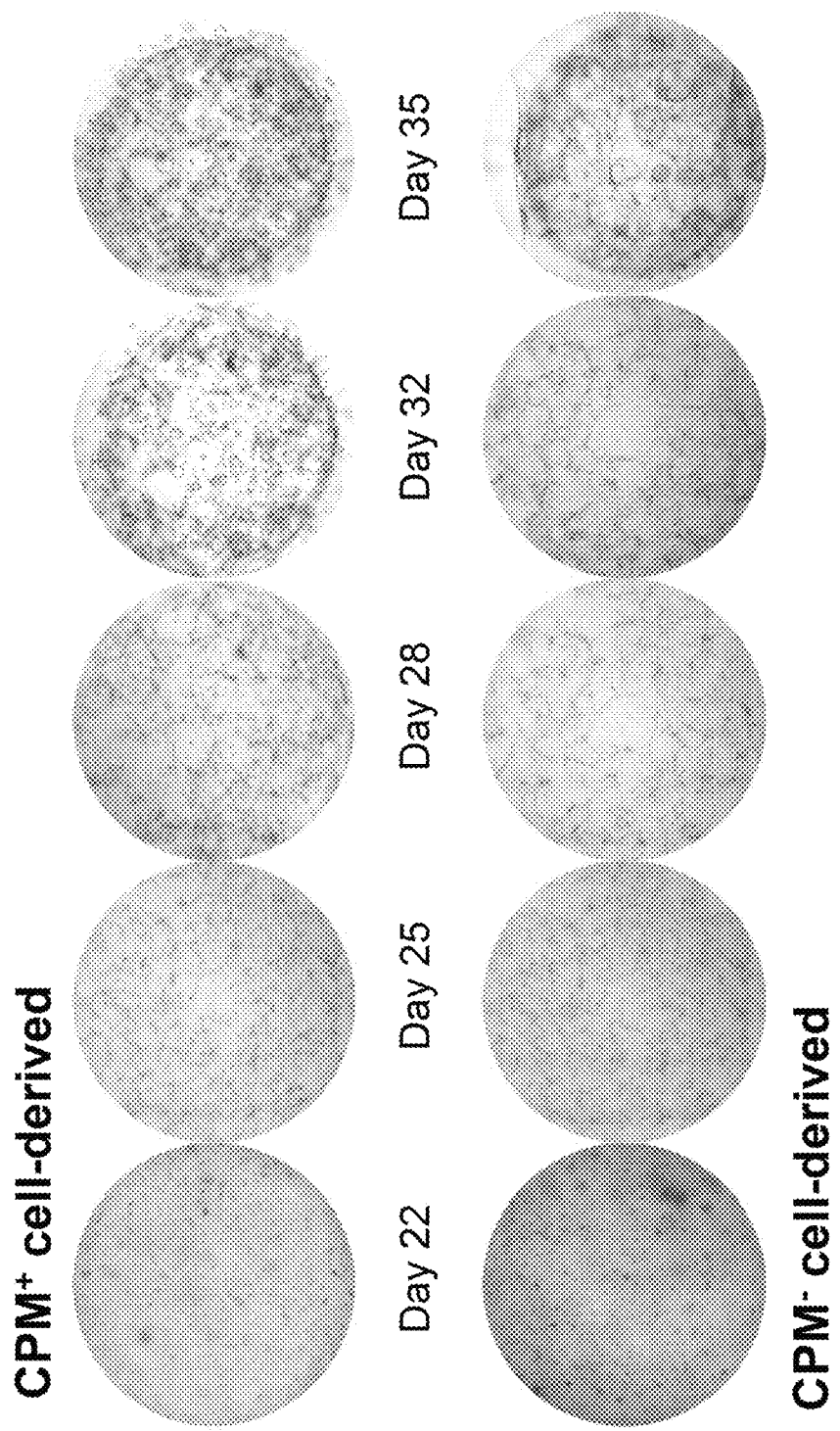
FIG. 5 shows the results of whole well imaging demonstrating a process comprising isolating CPM$^+$ cells (alveolar epithelial progenitor cells) separately from the control CPM$^-$ cells using the SFTPC (SFTPC-GFP) reporter iPS cells on Day 21 (i.e., upon completion of Step 4), subjecting the isolated cells to three-dimensional coculture with human fetal lung fibroblasts, and inducing type II alveolar epithelial cells from alveolar epithelial progenitor cells over a period of 14 days.

FIG. 5 shows the results of whole well imaging demonstrating a process comprising isolating CPM$^+$ cells (alveolar epithelial progenitor cells) separately from the control CPM$^-$ cells using the SFTPC (SFTPC-GFP) reporter iPS cells on Day 21 (i.e., upon completion of Step 4), subjecting the isolated cells to three-dimensional coculture with human fetal lung fibroblasts, and inducing type II alveolar epithelial cells from alveolar epithelial progenitor cells over a period of 14 days. The results indicate that both CPM$^+$ cells and CPM$^-$ cells formed spheroids with the elapse of time, and the spheroids were increased and enlarged. While CPM$^+$ cells became SFTPC-GFP-positive from Day 11 to Day 14, CPM$^-$ cells remained negative.

FIG. 6 shows photographs demonstrating the results of observation of spheroids formed from CPM$^+$ cells on Day 35 (i.e., upon completion of Step 5) in a high-power field. The results demonstrate that SFTPC-GFP$^+$ cells formed tubular structures.

Figure 7:
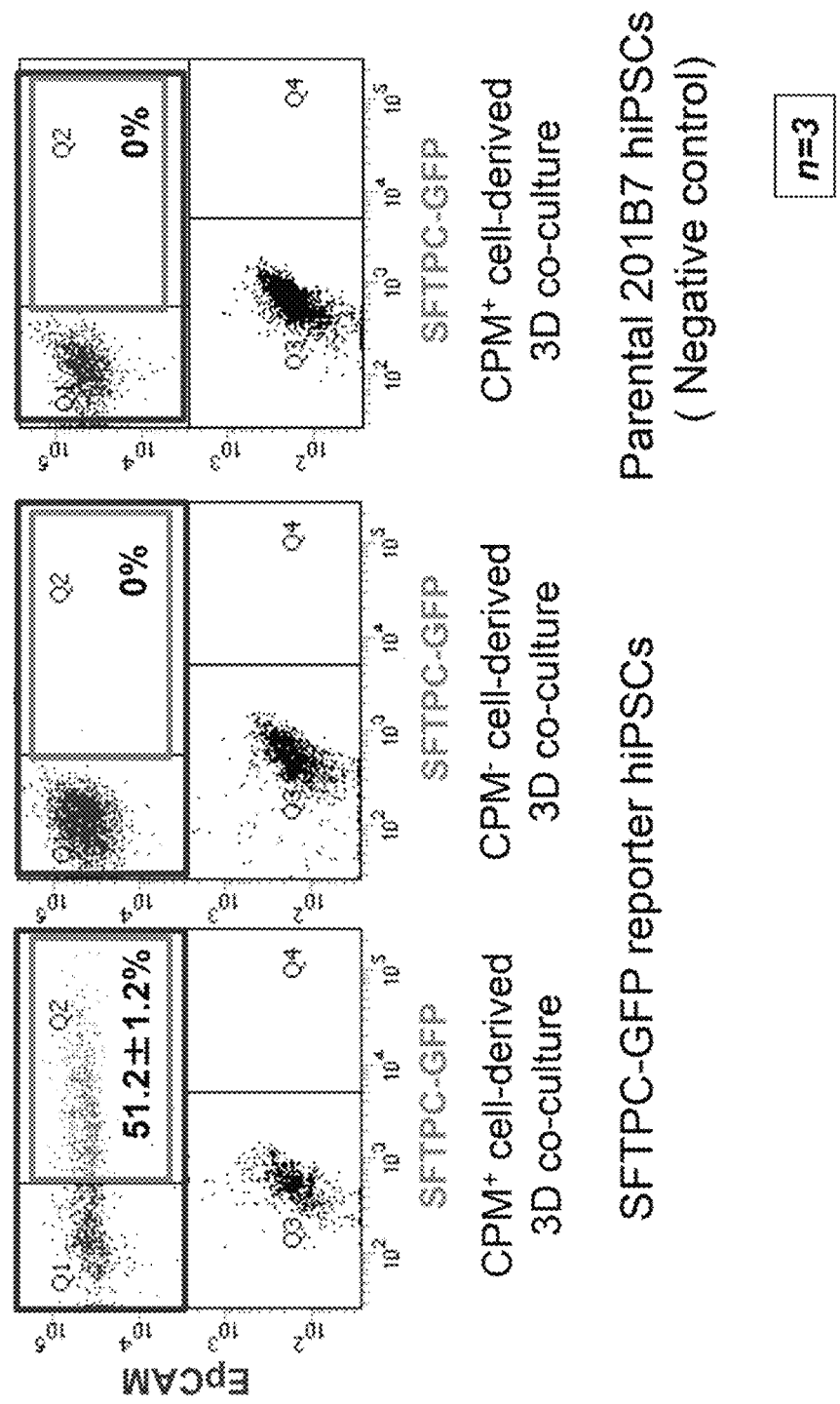
FIG. 7 shows the results of flow cytometry conducted on Day 35 (i.e., upon completion of Step 5) demonstrating that the proportion of SFTPC-GFP$^+$ cells (i.e., type II alveolar epithelial cells) reached 50% of the CPM$^+$ cell-derived EpCAM$^+$ cells.

FIG. 7 shows the results of flow cytometry conducted on Day 35 (i.e., upon completion of Step 5) demonstrating that the proportion of SFTPC-GFP$^+$ cells (i.e., type II alveolar epithelial cells) reached 50% of the CPM$^+$ cell-derived EpCAM$^+$ cells. Among the CPM$^-$ cell-derived EpCAM$^+$ cells, the percentage of SFTPC-GFP$^+$ cells was 0%. As the negative control, the human iPS cell line (201B7) in the state before reporter cells were prepared was used.

Figure 8:
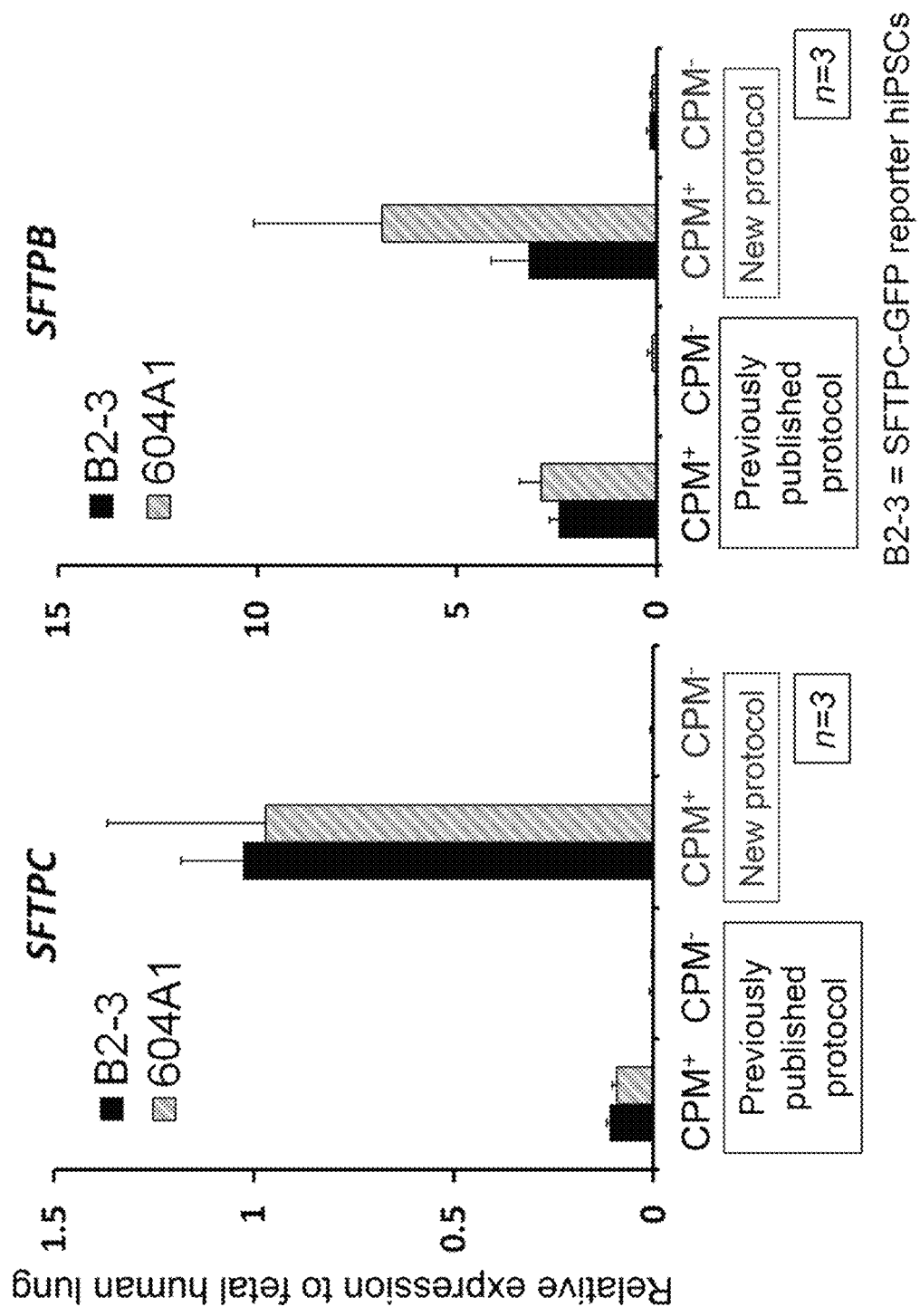
FIG. 8 demonstrates that both the SFTPC and SFTPB expression levels were increased by the method for type II alveolar epithelial cell induction shown in FIG. 1 (the new protocol), compared with the method described in Gotoh, S. et al., Stem Cell Reports, 2014, Vol. 3, pp. 394-403 (the previously published protocol).

FIG. 8 demonstrates that both the SFTPC and SFTPB expression levels were increased by the method for type II alveolar epithelial cell induction shown in FIG. 1 (the new protocol), compared with the method described in Gotoh, S. et al., Stem Cell Reports, 2014, Vol. 3, pp. 394-403 (the previously published protocol). "CPM$^+$" represents the gene expression of the three-dimensional co-culture product derived from CPM$^+$ cells and "CPM$^-$" represents the gene expression of the three-dimensional co-culture product derived from CPM$^-$ cells.

Figure 9:
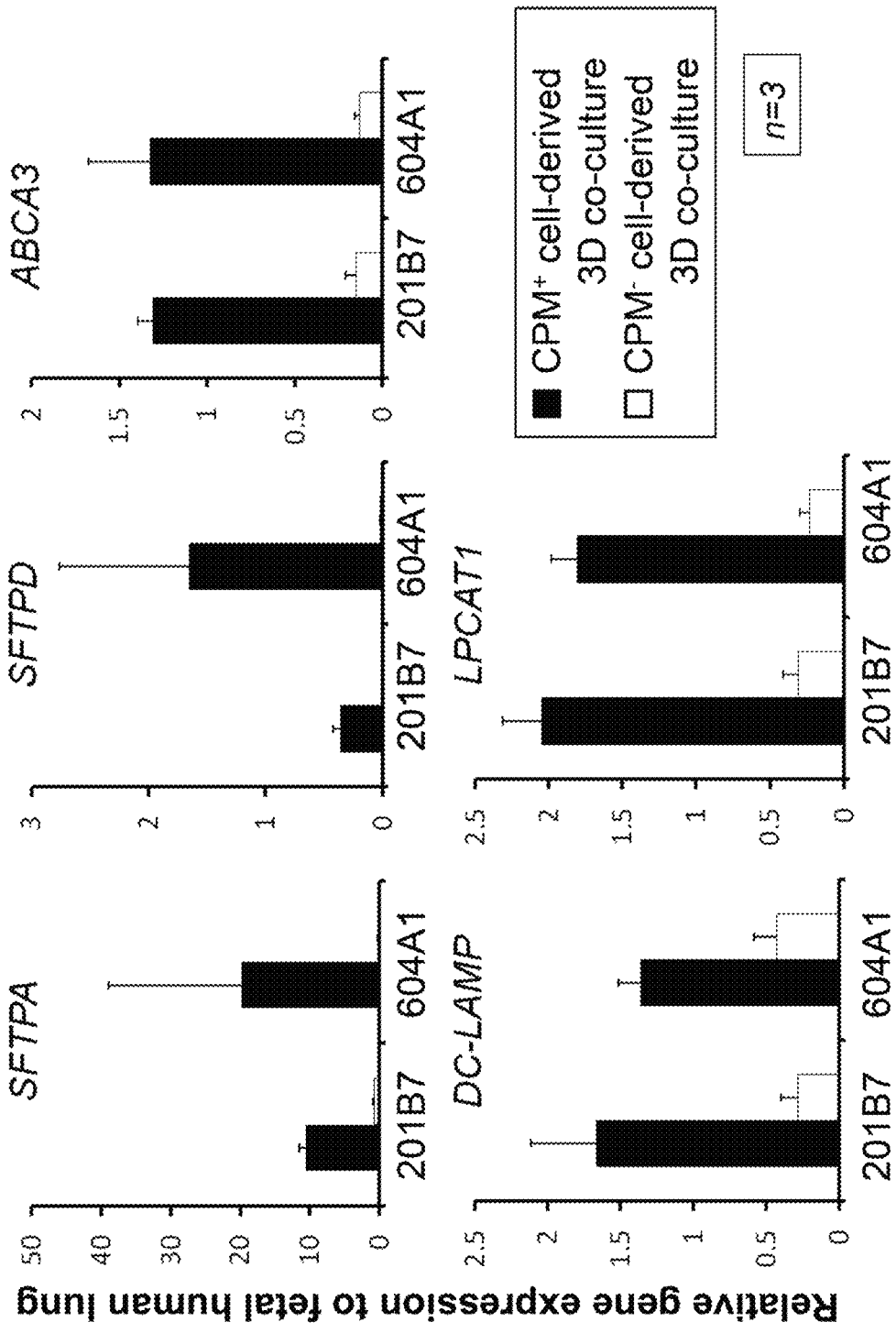
FIG. 9 demonstrates that various marker proteins for type II alveolar epithelial cells are expressed in a CPM$^+$ cell-derived three-dimensional culture product on Day 35 (i.e., upon completion of Step 5), in comparison with the case of a CPM$^-$ cell-derived three-dimensional culture product.

FIG. 9 demonstrates that various marker proteins for type II alveolar epithelial cells are expressed in a CPM$^+$ cell-derived three-dimensional culture product on Day 35 (i.e., upon completion of Step 5), in comparison with the case of a CPM$^-$ cell-derived three-dimensional culture product. The results demonstrate that many marker genes specific to type II alveolar epithelial cells, such as SFTPA and SFTPD as pulmonary surfactant proteins, DC-LAMP and ABCA3 localized in lamellar bodies that are morphologically characteristics of type II alveolar epithelial cells, and LPCAT1 known as an enzyme that synthesizes a lipid contained in a surfactant were expressed in CPM cell-derived three-dimensional culture products.

Figure 10:
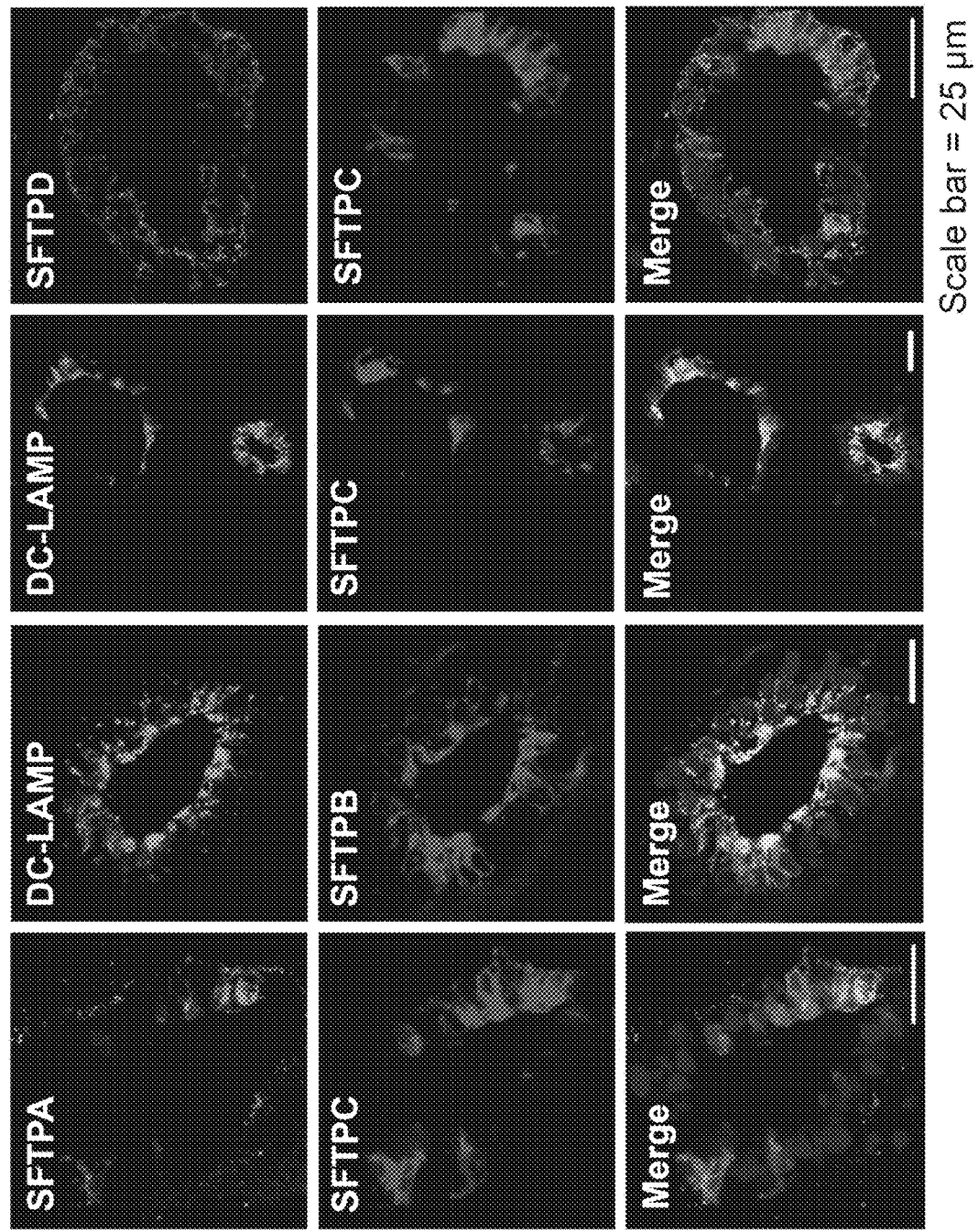
FIG. 10 shows double fluorescent immunostaining images of spheroids on Day 35 (i.e., upon completion of Step 5).

FIG. 10 shows double fluorescent immunostaining images of spheroids on Day 35 (i.e., upon completion of Step 5). FIG. 10 shows that various surfactant proteins (i.e., SFTPA, SFTPB, SFTPC, and SFTPD) were expressed in cells in tubular forms and that DC-LAMP as a lamellar body marker was localized particularly on the tubular side.

Figure 11:
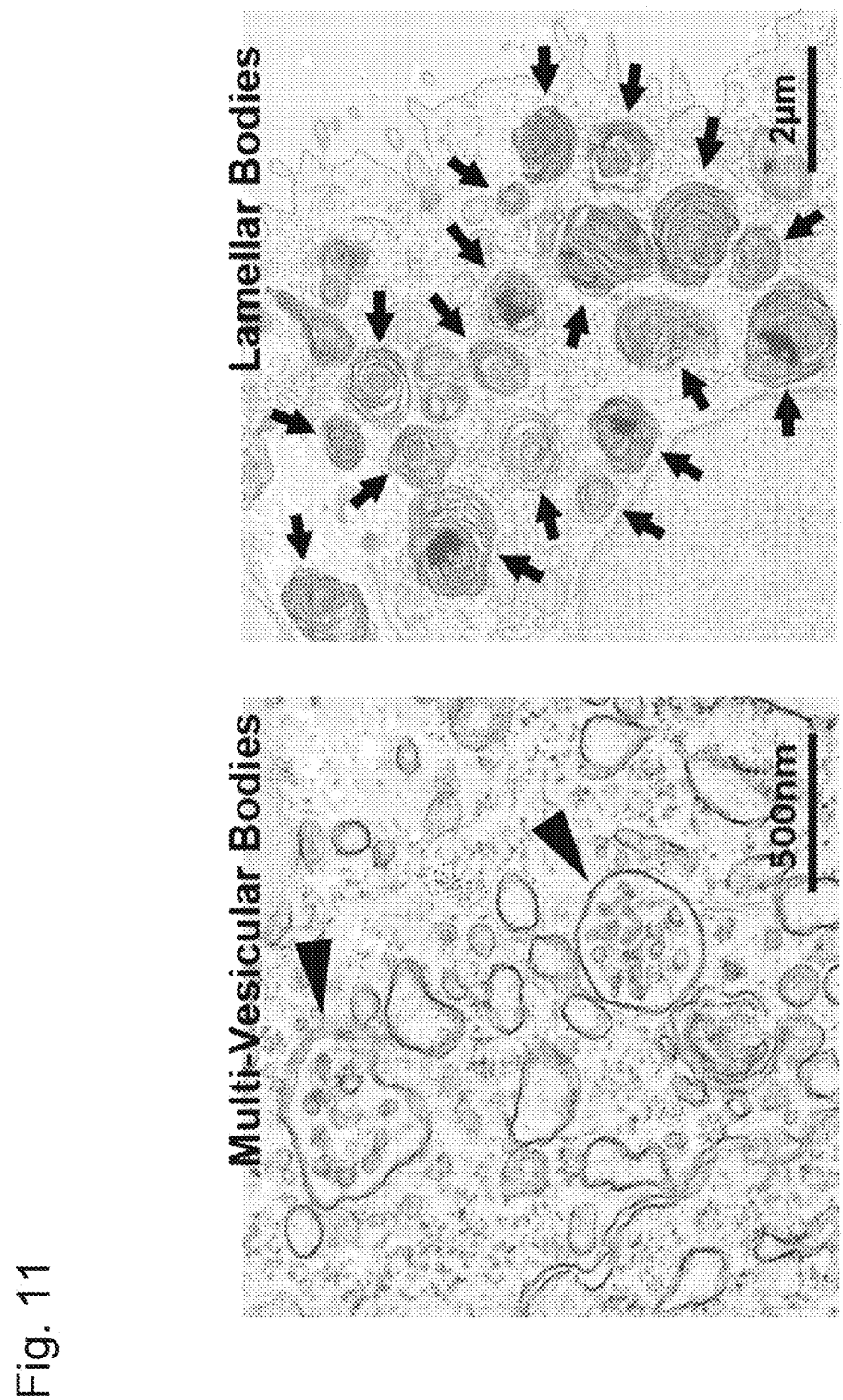
FIG. 11 shows transmission electron microscopic images of spheroids on Day 35 (i.e., upon completion of Step 5).

FIG. 11 shows transmission electron microscopic images of spheroids on Day 35 (i.e., upon completion of Step 5). Many lamellar bodies characteristics of type II alveolar epithelial cells were formed (the photograph on the right) and multi-vesicular bodies as progenitors thereof were also observed (the photograph on the left).

[Example 2] Method for Type II Alveolar Epithelial Cell Culture

1. Three-Dimensional Subculture of Type II Alveolar Epithelial Cells

Figure 12:
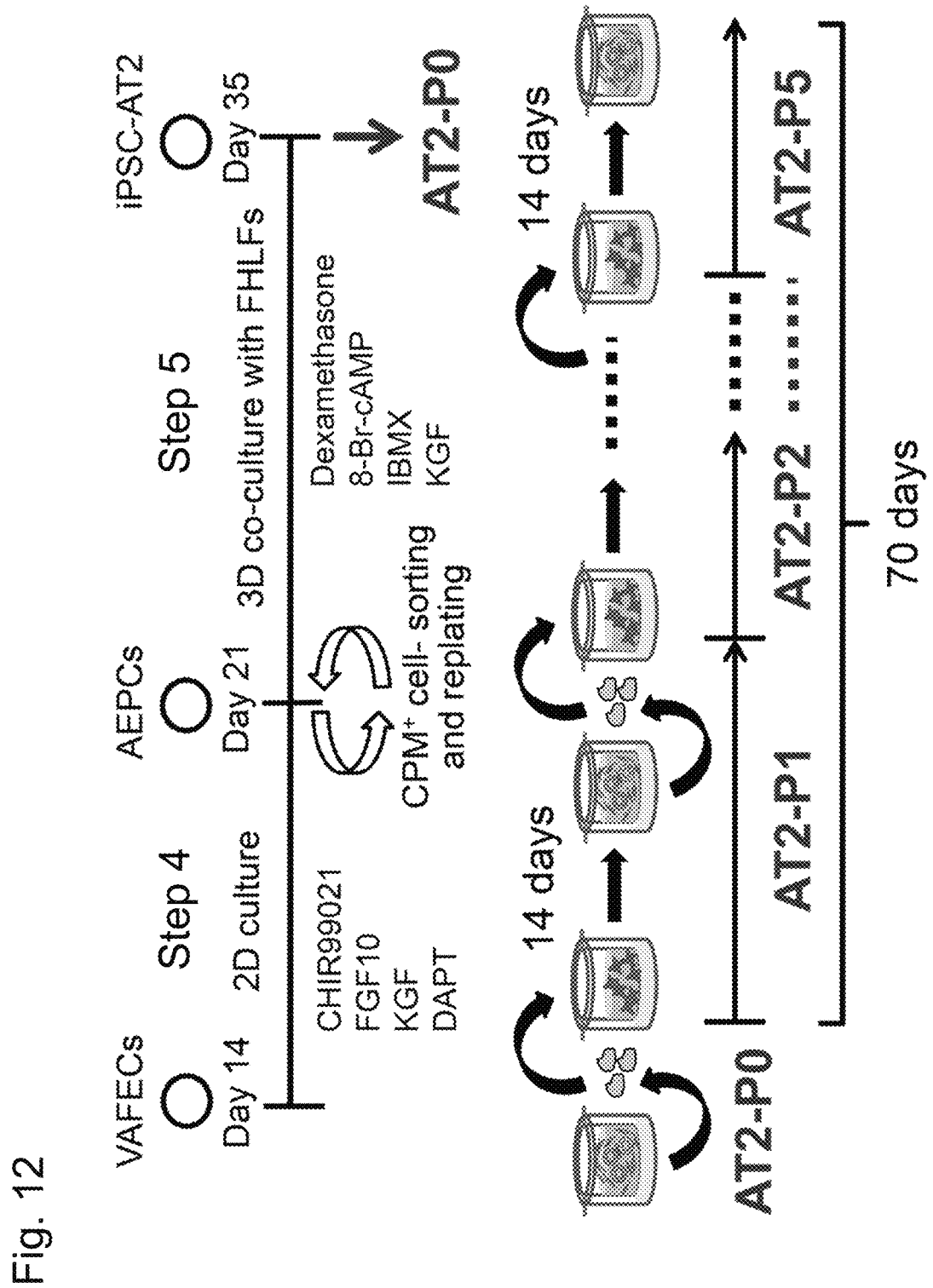
FIG. 12 shows a method for culturing the type II alveolar epithelial cells induced from human pluripotent stem cells via subculture in a three-dimensional coculture system over a long period of time.

FIG. 12 shows a method for culturing the type II alveolar epithelial cells induced from human pluripotent stem cells via subculture in a three-dimensional coculture system over a long period of time.

On Day 35 of type II alveolar epithelial cell induction in Example 1 (i.e., upon completion of Step 5), the cell mass composed of fibroblasts and spheroids subjected to three-dimensional coculture was removed from the Cell Culture Inserts. The removed cell mass was cut into small pieces of approximately 1 mm with the use of a clean surgical knife, the cells were recovered with the addition of PBS, and centrifugation was carried out at 900 rpm for 5 minutes to remove the supernatant. 0.1% Trypsin/EDTA was added to the precipitate and incubation was then carried out at 37° C. for 15 minutes while adequately repeating pipetting.

Subsequently, DMEM supplemented with 2% FBS was added to neutralize trypsin, followed by centrifugation at 4° C. and 900 rpm for 7 minutes. The supernatant was suction-removed, 1% BSA/PBS was added to the remaining cell pellet, and the resultant was centrifuged again at 4° C. and 900 rpm for 5 minutes. The cell pellet was suspended in 1% BSA/PBS, the mouse anti-human Ep-CAM antibody (Santa Cruz) was added thereto, and the reaction was allowed to proceed at 4° C. for 20 minutes.

Subsequently, the cells were washed 2 times with 1% BSA/PBS, the ALEXA FLUOR® 647-labeled anti-mouse antibody (Life Technologies) was added thereto, and the reaction was allowed to proceed at 4° C. for 20 minutes. After the reaction product was washed 2 times with 1% BSA/PBS, propidium iodide was added in the end, and SFTPC-GFP-positive cells were isolated via FACS with the use of BD FACSAria® II or Aria® III (BD Biosciences). The isolated cells were used as the type II alveolar epithelial cells (AT2-P0).

When type II alveolar epithelial cells were to be isolated without the use of reporter cells, the ALEXA FLUOR® 647-labeled anti-EpCAM antibody and LysoTracker® (Life Technologies) or a labeled antibody (e.g., a PE-labeled anti-CEACAM6 antibody) reacting with the known surface antigen of the type II alveolar epithelial cells (i.e., the AT2-antigen) were used to isolate EpCAM-positive, LysoTracker-positive, or AT2-antigen-positive cells via FACS.

When type II alveolar epithelial cells were to be subcultured, the type II alveolar epithelial cells were mixed with human fetal lung fibroblasts immediately after isolation, or cryopreserved type II alveolar epithelial cells were mixed with human fetal lung fibroblasts at a ratio of 1:50, the cell suspension of the medium for Step 5 comprising the cells at a cell density of $2.5 \times 10^6$ cells/ml and Y-27632 at the final concentration of 10 µM was mixed with MATRIGEL® (Corning) at a ratio of 1:1 at a low temperature, the resultant was immediately added to the upper layer of the Cell Culture Inserts, and the medium for Step 5 was added to the lower layer. The amount to be added to the upper layer of the 12-well plate Cell Culture Inserts is preferably 200 to 400 µL and the amount to be added to the lower layer thereof is preferably 1 ml.

On the first 2 days after the subculture, Y-27632 was added to the medium for Step 5 to the final concentration of 10 µM. Thereafter, the medium for Step 5 of the lower layer was selectively exchanged with another medium every other day. The type II alveolar epithelial cells were isolated 14 days after the initiation of culture, and culture was continued by repeating the three-dimensional coculture with the human fetal lung fibroblasts. As a subculture goes on to the following generation, the cells were designated as AT2-P1, AT2-P2. . . .

In the medium for Step 5 supplemented with WIF1 (R&D Systems) or IGF2 (R&D Systems) at 300 ng/ml or 100 ng/ml, respectively, type II alveolar epithelial cells were maintained with higher efficiency, compared with culture in the medium supplemented with EGF (Wako), NRG1β (Peprotech), CHIR99021 (Axon Medchem) at 10 ng/ml, 20 ng/ml, 3 µM, respectively.

2. Results of Three-Dimensional Subculture of Type II Alveolar Epithelial Cells

As shown in FIG. 12, the type II alveolar epithelial cells obtained in Step 5 of differentiating type II alveolar epithelial cells from alveolar epithelial progenitor cells were defined as "AT2-P0," isolated, and subjected to three-dimensional coculture. It was thus confirmed that culture could be continued from AT2-P1 to AT2-P5 (Day 105).

Figure 13:
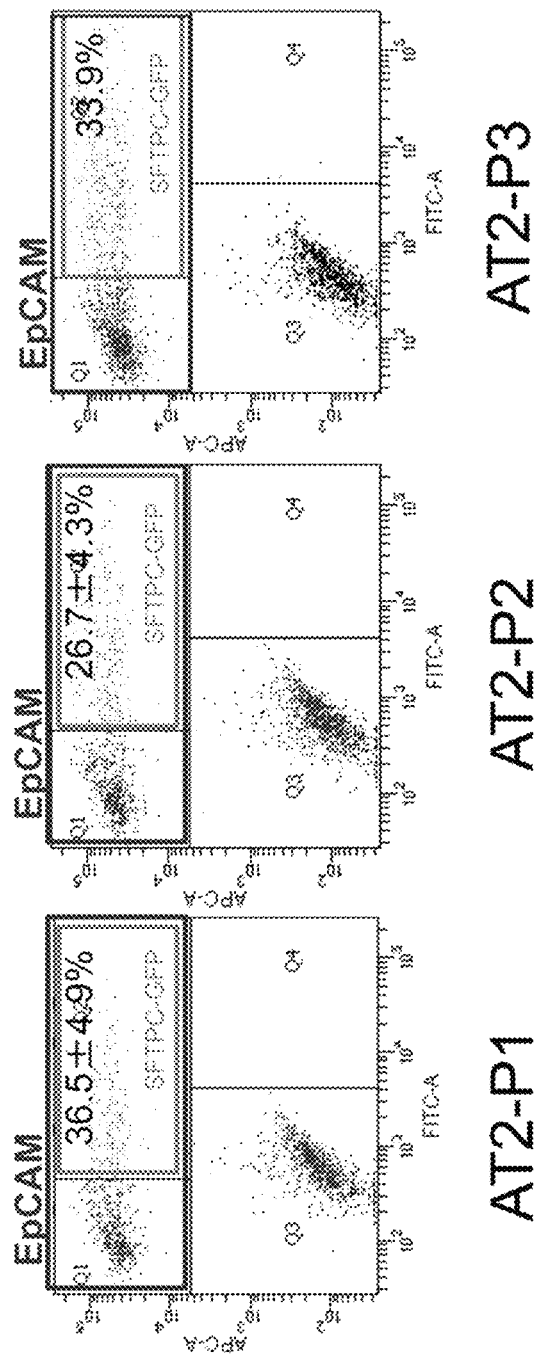
FIG. 13 demonstrates that SFTPC could be maintained at a certain positive rate via subculture of type II alveolar epithelial cells in a three-dimensional coculture system.

FIG. 13 demonstrates that SFTPC could be maintained at a certain positive rate via subculture of type II alveolar epithelial cells in a three-dimensional coculture system.

Figure 14:
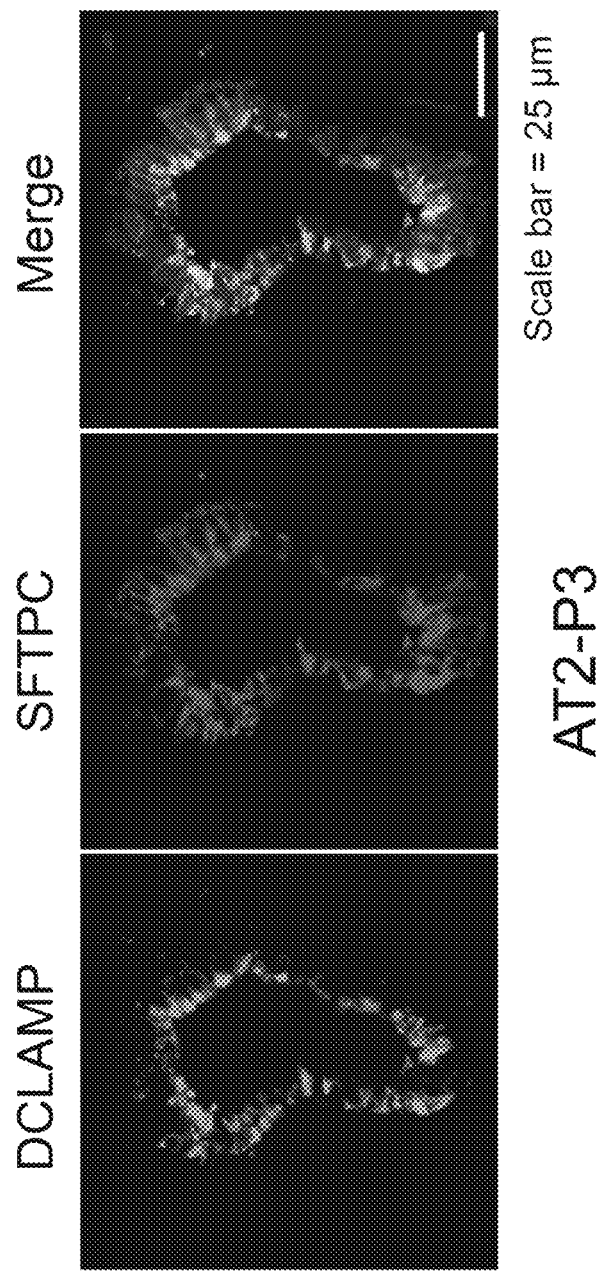
FIG. 14 shows double fluorescent immunostaining images demonstrating that the spheroids formed by the type II alveolar epithelial cells subjected to subculture (AT2-P3) also expressed DC-LAMP and SFTPC as with the case of spheroids at the AT2-P0 stage.

FIG. 14 shows double fluorescent immunostaining images demonstrating that the spheroids formed by the type II alveolar epithelial cells subjected to subculture (AT2-P3) also expressed DC-LAMP and SFTPC as with the case of spheroids at the AT2-P0 stage.

FIG. 15 demonstrates that type II alveolar epithelial cells were isolated via induction of differentiation with the use of the human iPS cell line (604A1) instead of SFTPC-GFP reporter cells up to Day 35 (i.e., upon completion of Step 5) and with the use of the anti-EpCAM antibody and LysoTracker® at the AT2-P0 stage.

Figure 15B:
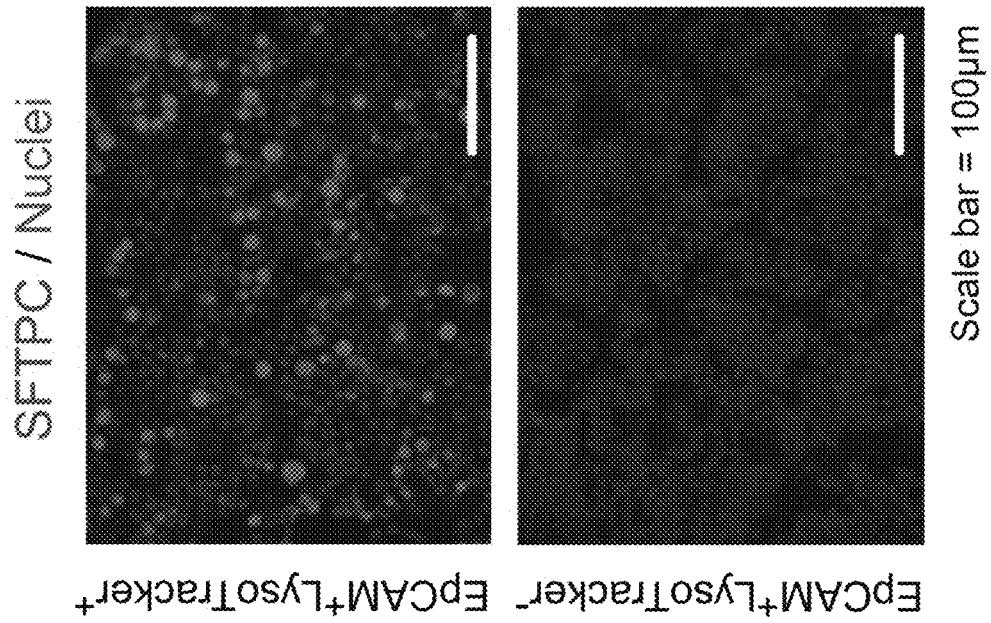
FIG. 15 demonstrates that type II alveolar epithelial cells were isolated via induction of differentiation with the use of the human iPS cell line (604A1) instead of SFTPC-GFP reporter cells up to Day 35 (i.e., upon completion of Step 5) and with the use of the anti-EpCAM antibody and LysoTracker® at the AT2-P0 stage.
Figure 15A:
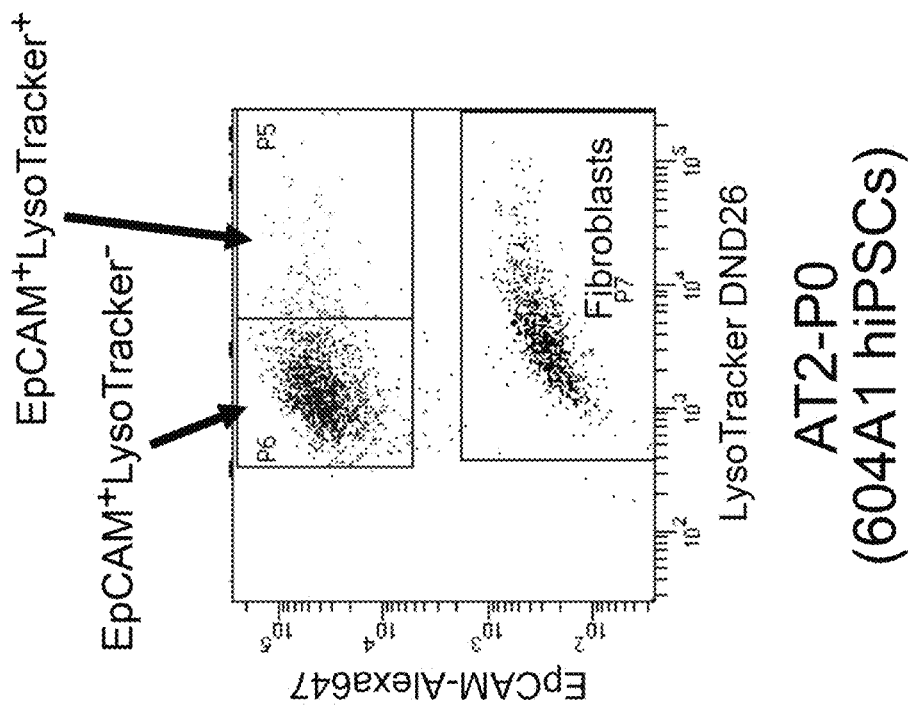

FIG. 15A and FIG. 15B demonstrate as follows.

FIG. 15A shows the results of flow cytometry conducted after dual staining with the use of the anti-EpCAM antibody and LysoTracker® DND26.

FIG. 15B shows the results of nuclear staining of EpCAM$^+$ LysoTracker®$^+$ cells and EpCAM$^+$ LysoTracker®$^{+-}$ cells isolated and allowed to adhere to glass slides via cytospinning while isolating and fluorescent immunostaining of SFTPC carried out simultaneously therewith. The results demonstrate that most SFTPC$^+$ cells were included in EpCAM$^+$ LysoTracker®$^+$ cells and SFTPC cells were not substantially included in EpCAM$^+$ LysoTracker®$^-$ cells.

FIG. 16 demonstrates that type II alveolar epithelial cells were isolated via induction of differentiation with the use of the human iPS cell line (604A1) instead of SFTPC-GFP reporter cells up to Day 35 (i.e., upon completion of Step 5) as with the case shown in FIG. 15 and with the use of the anti-CEACAM6 antibody at the AT2-P0 stage.

Figure 16A:
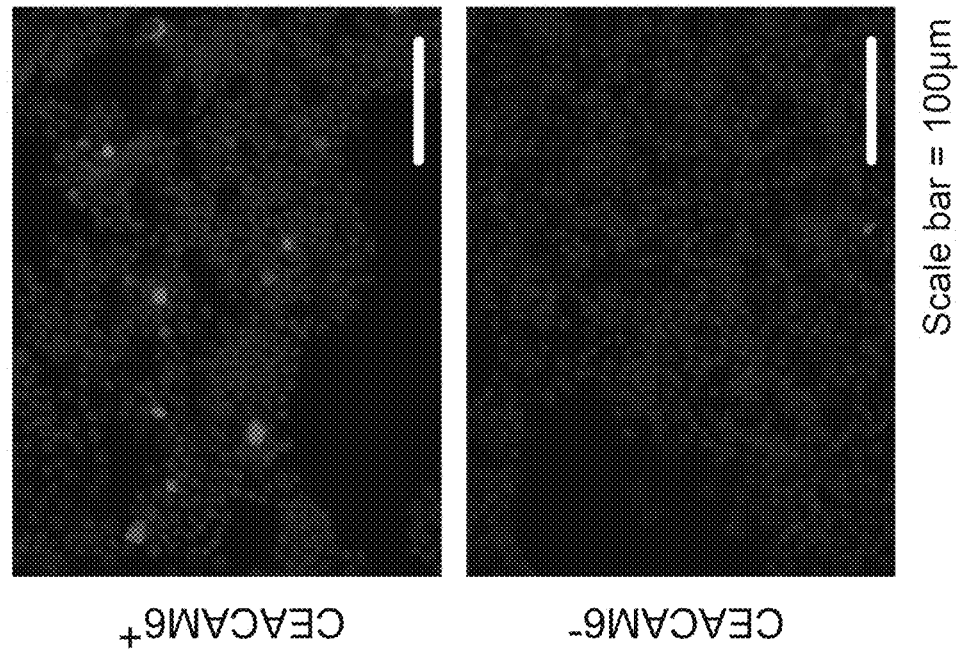
FIG. 16 demonstrates that type II alveolar epithelial cells were isolated via induction of differentiation with the use of the human iPS cell line (604A1) instead of SFTPC-GFP reporter cells up to Day 35 (i.e., upon completion of Step 5) as with the case shown in FIG. 15 and with the use of the anti-CEACAM6 antibody at the AT2-P0 stage.
Figure 16B:
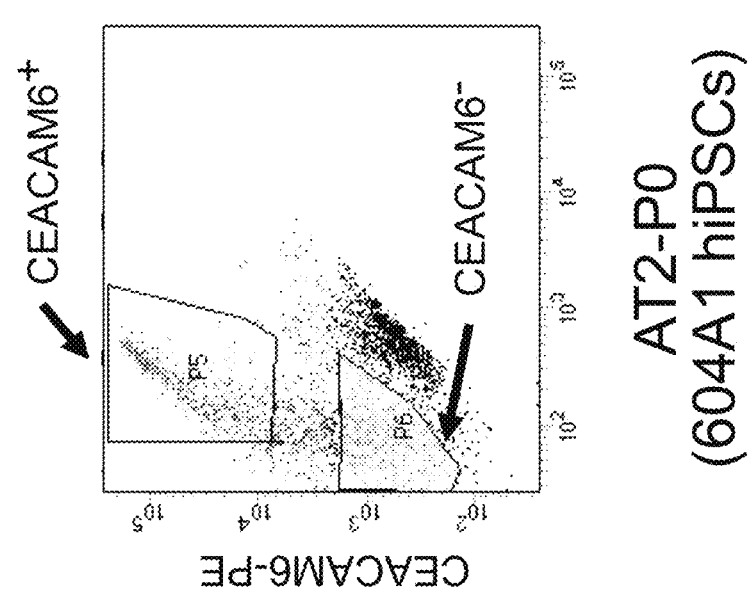

FIG. 16A and FIG. 16B demonstrate as follows.

FIG. 16A shows the results of flow cytometric analysis, following single staining with the use of the anti-CEACAM6 antibody.

FIG. 16B shows the results of nuclear staining of CEACAM6$^+$ cells and CEACAM6$^-$ cells isolated and allowed to adhere to glass slides via cytospinning and fluorescent immunostaining of SFTPC carried out simultaneously therewith. Not so much as the case shown in FIG. 15, most SFTPC cells were included in CEACAM6$^+$ cells, and SFTPC cells were not substantially included in CEACAM6$^-$ cells.

Figure 17:
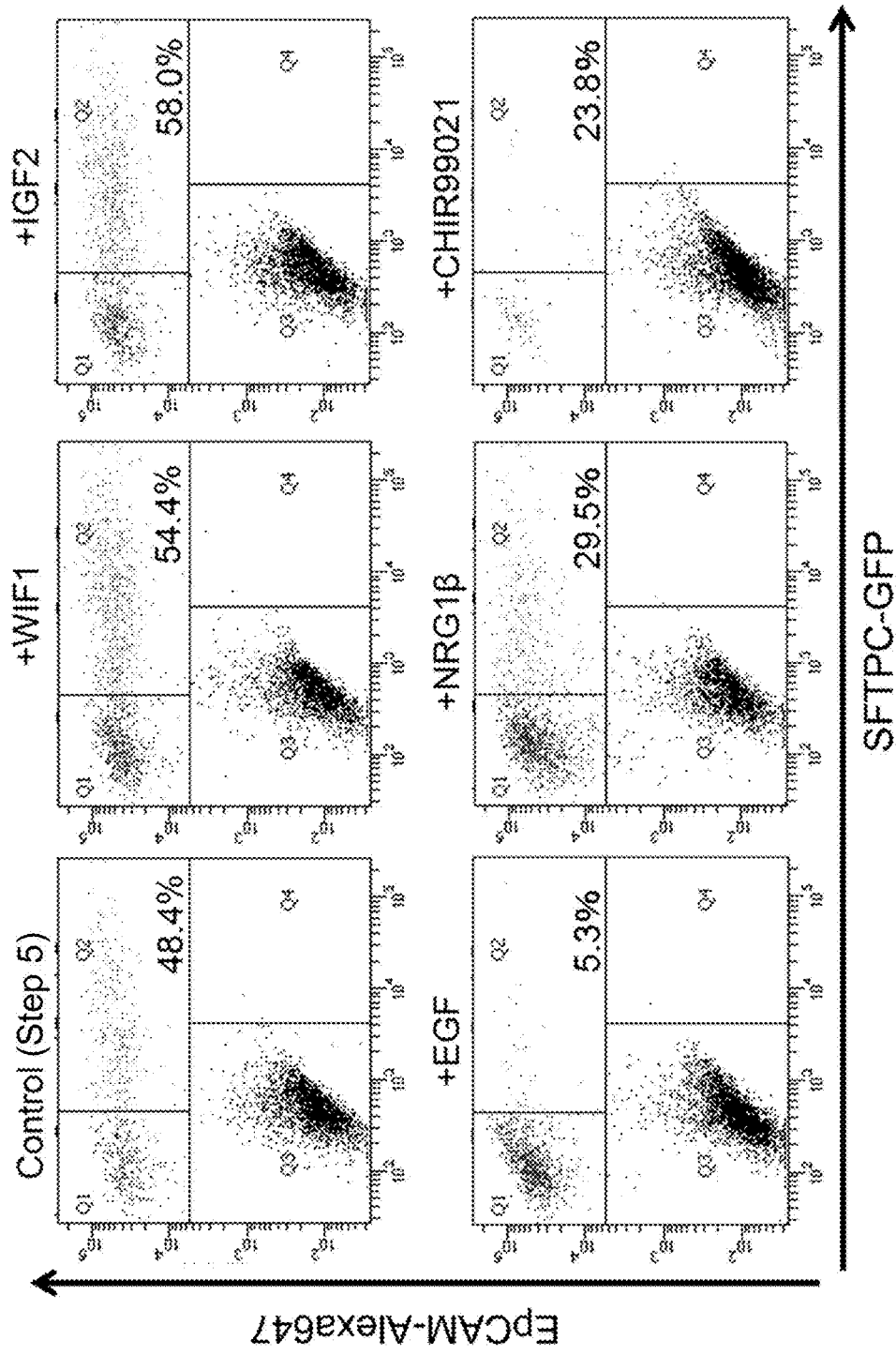
FIG. 17 demonstrates that type II alveolar epithelial cells were efficiently maintained in the medium for Step 5 supplemented with WIF1 (300 ng/ml) or IGF2 (100 ng/ml), when isolating AT2-P0 with the use of the SFTPC-GFP reporter cells and subjecting the isolated cells to subculture as shown in FIG. 12.

FIG. 17 demonstrates that type II alveolar epithelial cells were efficiently maintained in the medium for Step 5 supplemented with WIF1 (300 ng/ml) or IGF2 (100 ng/ml), when isolating AT2-P0 with the use of the SFTPC-GFP reporter cells and subjecting the isolated cells to subculture as shown in FIG. 12. In the case of the control experiment for cell maintenance in the medium for Step 5, the percentage of type II alveolar epithelial cells maintained in AT2-P1 was 48.4% relative to the epithelial cell component (9.4% of the whole including fibroblasts used for coculture). When various additives (300 ng/ml WIF, 100 ng/ml IGF2, 10 ng/ml EGF, 20 ng/ml NRG1 β, 3 μM CHIR99021) were added, in contrast, the percentages of type II alveolar epithelial cells maintained were 54.4%, 58.0%, 5.3%, 29.5%, and 23.8%, respectively, relative to the epithelial cell component (20.2%, 16.6%, 1.2%, 11.3%, and 0.5%, respectively, of the whole).

Figure 18:
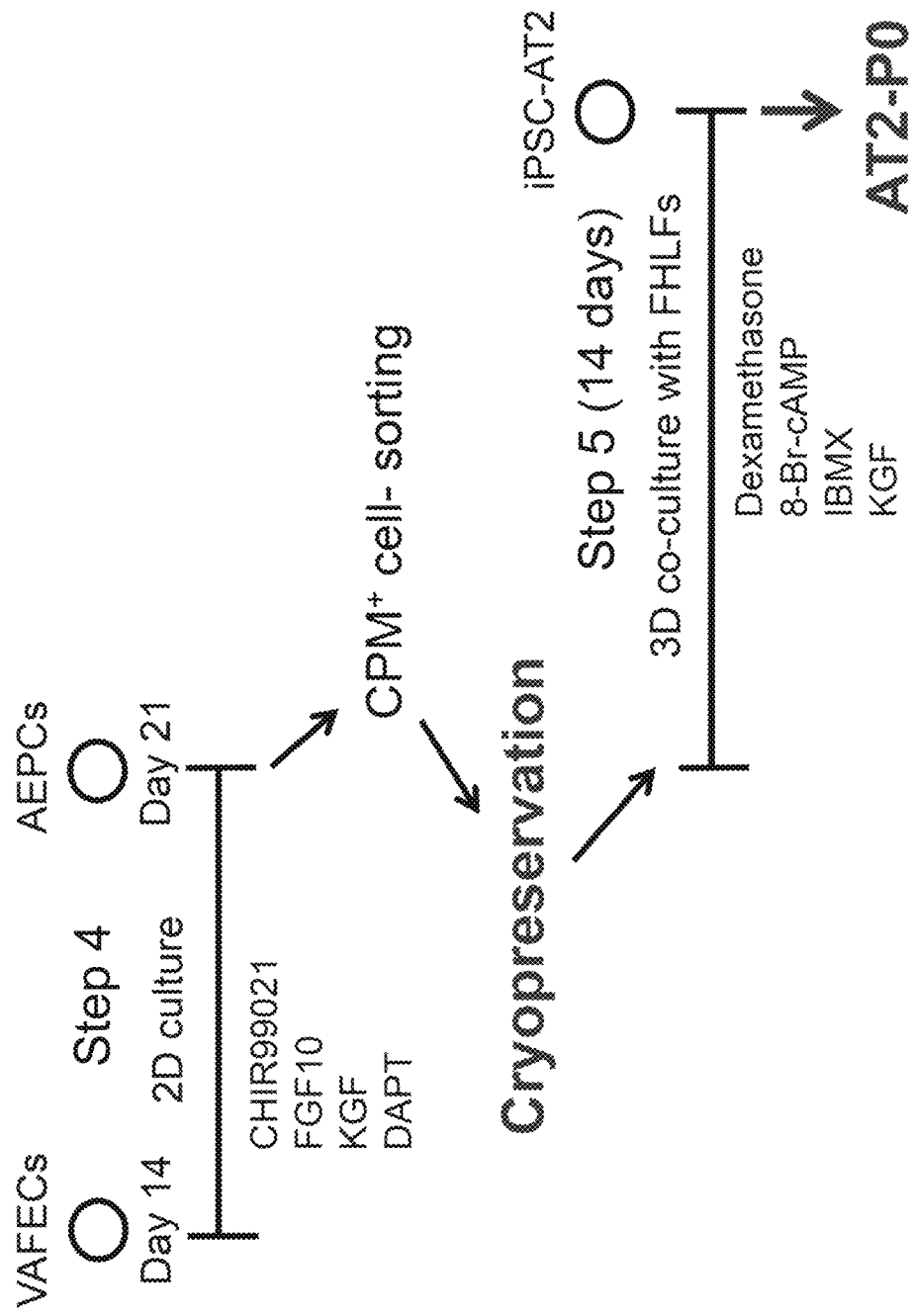
FIG. 18 shows a method for inducing type II alveolar epithelial cells by cryopreserving human alveolar epithelial progenitor cells on Day 21 (i.e., upon completion of Step 4) and subjecting the resulting cells to three-dimensional coculture.

[Example 3] Method for Storage of Alveolar Epithelial Progenitor Cells or Type II Alveolar Epithelial Cells 1. Method for Storage of Alveolar Epithelial Progenitor Cells or Type II Alveolar Epithelial Cells
1-1. Isolation of Alveolar Epithelial Progenitor Cells Via MACS and Cryopreservation Thereof FIG. 18 shows a method for inducing type II alveolar epithelial cells by cryopreserving human alveolar epithelial progenitor cells on Day 21 (i.e., upon completion of Step 4) and subjecting the resulting cells to three-dimensional coculture.

On Day 21 after the induction of type II alveolar epithelial cells in Example 1 (i.e., upon completion of Step 4), alveolar epithelial progenitor cells were isolated via magnetic activated cell sorting (MACS) with the use of antibodies reacting with CPM and then cryopreserved. In the same manner as with the isolation of alveolar epithelial progenitor cells via FACS in Example 1, the reaction was allowed to proceed to the treatment with the primary antibody using the mouse anti-human CPM antibody, and the reaction product was then washed 2 times with 1% BSA/PBS.

Thereafter, the microbead-labeled anti-mouse IgG1 antibody (Miltenyi Biotech) was added as the secondary antibody, and the reaction was allowed to proceed at 4° C. for 15 minutes. After the reaction product was washed 2 times with 0.5% BSA/PBS supplemented with 2 mM EDTA, CPM-positive cells were isolated via MACS using magnetic separation columns (Miltenyi Biotech), and MACS was repeated 2 times, so as to enhance the purity.

When the isolated alveolar epithelial progenitor cells were cryopreserved, $5.0 \times 10^5$ cells were suspended in 500 μl of a stock solution comprising dimethyl sulfoxide (DMSO) (Sigma-Aldrich) and the medium for Step 4 at a ratio of 1:9, the suspension was injected into a freezing vial (Nalgene), the vial was immediately introduced into a cell-freezing container (Nalgene), and the resultant was slowly frozen in a deep freezer at −80° C. over a period of 24 hours, followed by storage in a liquid nitrogen tank.

When the cryopreserved cells were to be thawed, a cell suspension was prepared with the rapid addition of 10 ml of the pre-heated medium for Step 4, the suspension was centrifuged at 900 rpm for 5 minutes, the supernatant was suction-removed, and the resultant was suspended again in the medium for Step 4.

1-2. Cryopreservation of Type II Alveolar Epithelial Cells

Figure 20:
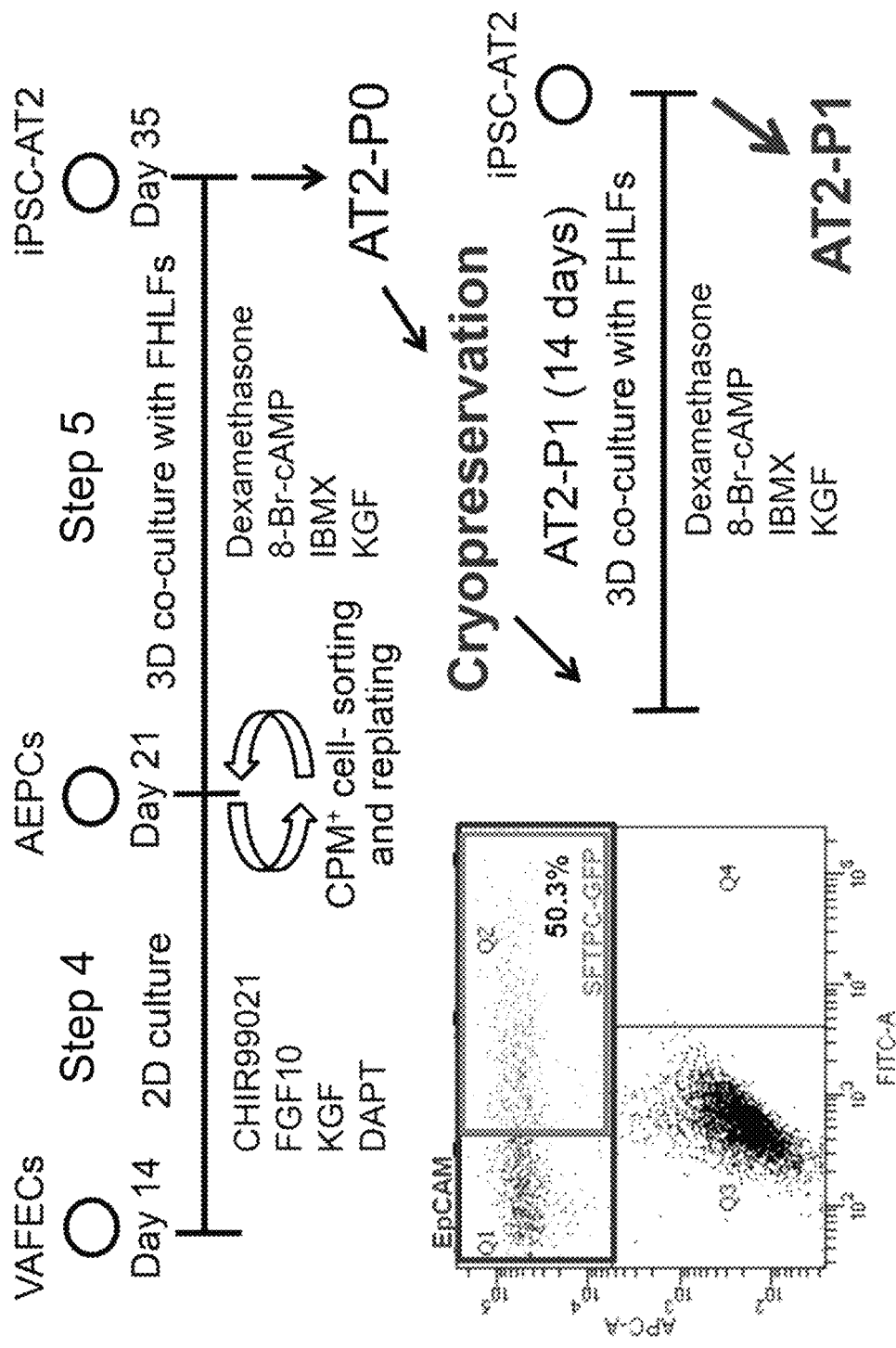
FIG. 20 shows a method for type II alveolar epithelial cell culture comprising cryopreserving type II alveolar epithelial cells and subjecting the resulting cells to three-dimensional coculture.

FIG. 20 shows a method for type II alveolar epithelial cell culture comprising cryopreserving type II alveolar epithelial cells and subjecting the resulting cells to three-dimensional coculture.

When the type II alveolar epithelial cells induced in Example 1 were isolated and then cryopreserved, $2.0 \times 10^5$ cells were suspended in 200 μl of a stock solution comprising DMSO and the medium for Step 5 at a ratio of 1:9, the suspension was injected into a freezing vial (Nalgene), the vial was immediately introduced into a cell-freezing container (Nalgene), and the resultant was slowly frozen in a deep freezer at −80° C. over a period of 24 hours, followed by storage in a liquid nitrogen tank.

When the cryopreserved cells were to be thawed, a cell suspension was prepared with the rapid addition of 10 ml of the pre-heated medium for Step 5, the suspension was centrifuged at 900 rpm for 5 minutes, the supernatant was suction-removed, and the resultant was suspended again in the medium for Step 5.

Figure 19:
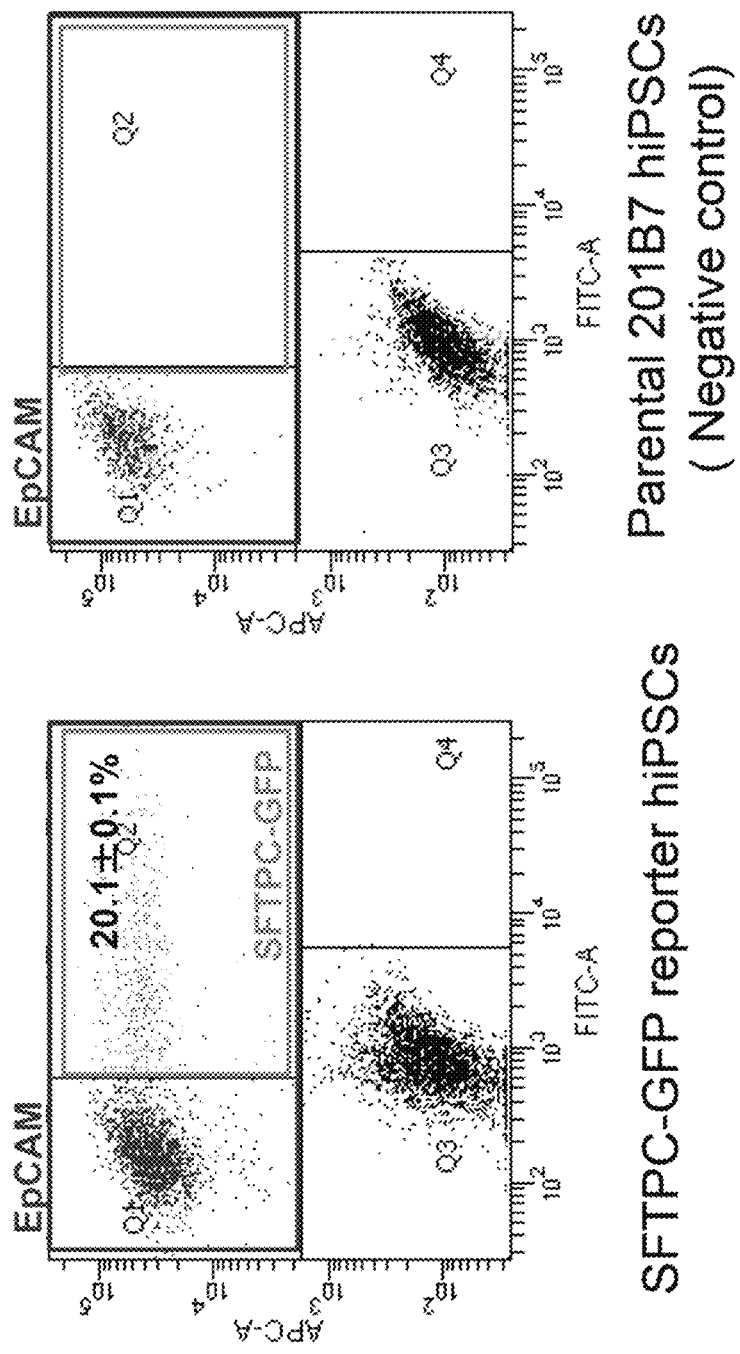
FIG. 19 demonstrates that type II alveolar epithelial cells were differentiated from the cryopreserved alveolar epithelial progenitor cells with an efficiency of approximately 20% as a result of the process shown in FIG. 18.

2. Results of Storage of Alveolar Epithelial Progenitor Cells or Type II Alveolar Epithelial Cells
2-1. Results of Storage of Alveolar Epithelial Progenitor Cells FIG. 19 demonstrates that type II alveolar epithelial cells were differentiated from the cryopreserved alveolar epithelial progenitor cells with an efficiency of approximately 20% as a result of the process shown in FIG. 18.

2-2. Results of Storage of Type II Alveolar Epithelial Cells

As shown in FIG. 20, type II alveolar epithelial cells were cryopreserved, and three-dimensional coculture was carried out with the use of the resulting cells. Thus, culture was carried out while maintaining SFTPC with a constant positive rate.

INDUSTRIAL APPLICABILITY

According to the present invention, type II alveolar epithelial cells can be efficiently produced from pluripotent stem cells, and type II alveolar epithelial cells can be maintained.

All publications, patents, and patent applications cited herein are incorporated herein by reference in their entirety.

The invention claimed is:

1. A method for producing a cell population comprising type II alveolar epithelial cells from pluripotent stem cells comprising Steps (1) to (5) below:
   (1) culturing pluripotent stem cells in a medium containing activin A and a glycogen synthase kinase 3β (GSK3β) inhibitor;
   (2) culturing the cells obtained in Step (1) in a medium containing a morphogenetic protein (BMP) inhibitor and a transforming growth factor beta (TGFβ) inhibitor;
   (3) culturing the cells obtained in Step (2) in a medium containing bone morphogenetic protein 4 (BMP4), retinoic acid, and a GSK3β inhibitor;
   (4) culturing the ventral anterior foregut cells obtained in Step (3) in a medium containing a GSK3β inhibitor, Fibroblast Growth Factor 10 (FGF10), keratinocyte growth factor (KGF), and a NOTCH signal inhibitor for a duration of time until alveolar epithelial progenitor cells are induced; followed by a step of isolating carboxypeptidase M-positive (CPM-positive) cells as alveolar epithelial progenitor cells; and
   (5) subjecting the induced alveolar epithelial progenitor cells obtained in Step (4) to three-dimensional culture in a basal medium supplemented with additives consisting of a steroid drug, a cAMP derivative, a phosphodiesterase inhibitor, and KGF;
   following Step (5), a further step of isolating cells positive for one or more type II alveolar epithelial cell markers selected from the group consisting of surfactant protein C (SFTPC), epithelial cell adhesion molecule (EpCAM), and carcinoembryonic antigen-related cell adhesion molecule 6 (CEACAM6) as type II alveolar epithelial cells;
   wherein cells positive for staining of acidic fractions for live cells are isolated as type II alveolar epithelial cells;
   thereby obtaining a cell population wherein the type II alveolar epithelial cells are at least 50% of the cell population, relative to total epithelial cells.

2. The method according to claim 1, wherein the GSK3β inhibitor is CHIR99021, the BMP inhibitor is Noggin, the TGFβ inhibitor is SB431542, the NOTCH signal inhibitor is N—[N-(3,5-Difluorophenylacetyl-L-alanyl)]-S-phenylglycine t-Butyl ester (DAPT), the steroid drug is dexamethasone, the cAMP derivative is 8-Br-cAMP, and the phosphodiesterase inhibitor is 3-isobutyl-1-methylxanthine (IBMX).

3. The method according to claim 1, wherein the medium of Step (1) further comprises Rho kinase (ROCK) inhibitor and/or a histone deacetylase (HDAC) inhibitor.

4. The method according to claim 3, wherein the ROCK inhibitor is Y-27632 and/or the HDAC inhibitor is sodium butyrate.

5. The method according to claim 1, wherein, following Step (4), the alveolar epithelial progenitor cells are cryopreserved and the alveolar epithelial progenitor cells cultured in Step (5) are obtained by thawing the cryopreserved alveolar epithelial progenitor cells.

6. The method according to claim 1, wherein the medium of Step (5) further comprises a ROCK inhibitor.

7. The method according to claim 6, wherein the ROCK inhibitor is Y-27632.

8. The method according to claim 1, wherein, following Step (5), the type II alveolar epithelial cells obtained are cryopreserved.

9. The method according to claim 1, wherein the alveolar epithelial progenitor cells induced in Step (4) are carboxypeptidase M-positive (CPM-positive).

10. The method according to claim 1, wherein the culturing of Step (1) is for at least 6 days; the culturing of Step (2) is for at least 2 days; the culturing of Step (3) is for at least 4 days; the culturing of Step (4) is for at least 4 days; and the culturing of Step (5) is for at least 14 days.

11. The method according to claim 1, wherein the activin A and the GSK3β inhibitor are present in the medium of Step (1) at concentrations, respectively, of 100 ng/ml and 1 μM;
   wherein the BMP and TGFβ inhibitor are present in the medium of Step (2) at concentrations, respectively, of 100 ng/ml and 10 μM;
   wherein the BMP4, retinoic acid and the GSK3β inhibitor are present in the medium of Step (3) at concentrations, respectively, of 20 ng, 0.05 μM and; 3 μM;
   wherein the GSK3β inhibitor, FGF10, KGF and NOTCH signal inhibitor are present in the medium of Step (4) at concentrations, respectively of, 3 μM, 10 ng/ml, 10 ng/ml, and 20 μM,
   wherein the steroid drug, cAMP derivative, phosphodiesterase inhibitor, and the KGF are present in the medium of Step (5) at concentrations, respectively, of 50 nM, 100 μM, 100 μM, and 10 ng/ml, without any GSK3 β inhibitor and without any FGF10;
   wherein the culturing of Step (1) is for 6 days; the culturing of Step (2) is for 2 to 4 days; the culturing of Step (3) is for 4 to 6 days; the culturing of Step (4) is for 4 to 14 days; and the culturing of Step (5) is for 14 days, and
   wherein the GSK3 β inhibitor is CHIR99021, the BMP inhibitor is Noggin, the TGFβ inhibitor is SB431542, the NOTCH signal inhibitor is N—[N-(3,5-Difluorophenylacetyl-Lalanyl)]-S-phenylglycine t-Butyl ester (DAPT), the steroid drug is dexamethasone, the cAMP derivative is 8-Br-cAMP, the retinoic acid is all-trans retinoic acid (ATRA), and the phosphodiesterase inhibitor is 3-isobutyl-1-methylxanthine (IBMX).

12. The method according to claim 1, wherein the activin A and the GSK3 β inhibitor are present in the medium of Step (1) at concentrations, respectively, of 100 ng/ml and 1 μM;
   wherein the BMP and TGFβ inhibitor are present in the medium of Step (2) at concentrations, respectively, of 100 ng/ml and 10 μM;
   wherein the BMP4, retinoic acid and the GSK3β inhibitor are present in the medium of Step (3) at concentrations, respectively, of 20 to 100 ng/ml, 0.05 to 1 μM and 2.5 to 3.5 μM;
   wherein the GSK3β inhibitor, FGF10, KGF and NOTCH signal inhibitor are present in the medium of Step (4) at concentrations, respectively of, 1 to 3 μM, 10 to 100 ng/ml, 10 ng/ml and 10 to 50 μM;
   wherein the steroid drug, cAMP derivative, phosphodiesterase inhibitor, and the KGF are present in the medium of Step (5) at concentrations, respectively, of 50 nM, 100 μM, 100 μM and 10 to 100 ng/ml;

wherein the culturing of Step (1) is for 6 days; the culturing of Step (2) is for 2 to 4 days; the culturing of Step (3) is for 4 to 6 days; the culturing of Step (4) is for 4 to 14 days; and the culturing of Step (5) is for 14 days, and wherein the GSK3 β inhibitor is CHIR99021, the BMP inhibitor is Noggin, the TGFβ inhibitor is SB431542, the NOTCH signal inhibitor is N—[N-(3,5-Difluoro-phenylacetyl-Lalanyl)]-S-phenylglycine t-Butyl ester (DAPT), the steroid drug is dexamethasone, the cAMP derivative is 8-Br-cAMP, and the phosphodiesterase inhibitor is 3-isobutyl-1-methylxanthine (IBMX).

13. The method according to claim 1, wherein the activin A and the GSK3β inhibitor are present in the medium of Step (1) at concentrations, respectively, of 100 ng/ml and 1 µM;

wherein the BMP and TGFβ inhibitor are present in the medium of Step (2) at concentrations, respectively, of 100 ng/ml and 10 µM;

wherein the BMP4, retinoic acid and the GSK3β inhibitor are present in the medium of Step (3) at concentrations, respectively, of 20 ng/ml, 1 µM and 2.5 to 3.5 µM;

wherein the GSK3β inhibitor, FGF10, KGF and NOTCH signal inhibitor are present in the medium of Step (4) at concentrations, respectively, of, 3 µM, 10 ng/ml, 10 ng/ml and 20 µM;

wherein the steroid drug, cAMP derivative, phosphodiesterase inhibitor, and the KGF are present in the medium of Step (5) at concentrations, respectively, of 50 nM, 100 µM, 100 µM and 10 ng/ml;

wherein the culturing of Step (1) is for 6 days; the culturing of Step (2) is for 2 to 4 days; the culturing of Step (3) is for 4 to 6 days; the culturing of Step (4) is for 4 to 14 days; and the culturing of Step (5) is for 14 days, and wherein the GSK3 β inhibitor is CHIR99021, the BMP inhibitor is Noggin, the TGFβ inhibitor is SB431542, the NOTCH signal inhibitor is N—[N-(3,5-Difluoro-phenylacetyl-Lalanyl)]-S-phenylglycine t-Butyl ester (DAPT), the steroid drug is dexamethasone, the cAMP derivative is 8-Br-cAMP, and the phosphodiesterase inhibitor is 3-isobutyl-1-methylxanthine (IBMX).

14. The method of claim 1, wherein:

the medium of Step (1) is a basal medium supplemented with additives consisting of the activin A and the glycogen synthase kinase 3β (GSK3β) inhibitor;

the medium of Step (2) is a basal medium supplemented with additives consisting of the BMP inhibitor and the TGFβ inhibitor; and the medium of Step (3) is a basal medium supplemented with additives consisting of the BMP4, the retinoic acid, and the GSK3β inhibitor.

* * * * *